United States Patent
Dey et al.

(10) Patent No.: US 11,952,363 B2
(45) Date of Patent: Apr. 9, 2024

(54) PIPERAZINE COMPOUNDS FOR THE TREATMENT OF AUTOIMMUNE DISEASE

(71) Applicant: Hoffmann-La Roche Inc., Little Falls, NJ (US)

(72) Inventors: Fabian Dey, Basel (CH); Zongxing Qiu, Shanghai (CN); Wei Zhu, Shanghai (CN); Ge Zou, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 705 days.

(21) Appl. No.: 17/262,170

(22) PCT Filed: Jul. 22, 2019

(86) PCT No.: PCT/EP2019/069609
§ 371 (c)(1),
(2) Date: Jan. 21, 2021

(87) PCT Pub. No.: WO2020/020800
PCT Pub. Date: Jan. 30, 2020

(65) Prior Publication Data
US 2021/0269423 A1    Sep. 2, 2021

(30) Foreign Application Priority Data

Jul. 23, 2018 (WO) ................ PCT/CN2018/096661

(51) Int. Cl.
  C07D 401/14      (2006.01)
  C07D 471/04      (2006.01)
  C07D 498/08      (2006.01)

(52) U.S. Cl.
  CPC ......... *C07D 401/14* (2013.01); *C07D 471/04* (2013.01); *C07D 498/08* (2013.01)

(58) Field of Classification Search
  CPC ... C07D 401/14; C07D 471/04; C07D 498/08
  See application file for complete search history.

(56) References Cited

U.S. PATENT DOCUMENTS

2019/0185469 A1    6/2019    Dyckman et al.

FOREIGN PATENT DOCUMENTS

| WO | WO-2005040136 A1 * | 5/2005 | ........... C04B 35/632 |
|---|---|---|---|
| WO | 2013/180066 | 12/2013 | |
| WO | 2015/057655 A1 | 4/2015 | |
| WO | 2015/057659 A1 | 4/2015 | |
| WO | 2019/028302 A1 | 2/2017 | |
| WO | 2017/106607 A1 | 6/2017 | |
| WO | 2018/005586 A1 | 1/2018 | |
| WO | 2018/026620 A1 | 2/2018 | |
| WO | 2018/031434 A1 | 2/2018 | |
| WO | 2018/047081 A1 | 3/2018 | |
| WO | 2018/049089 A1 | 3/2018 | |
| WO | 2019/018354 A1 | 1/2019 | |
| WO | 2019/028301 A1 | 2/2019 | |
| WO | 2019/099336 A1 | 5/2019 | |
| WO | 2019/118799 A1 | 6/2019 | |
| WO | 2019/123294 A2 | 6/2019 | |
| WO | 2019/125849 A1 | 6/2019 | |
| WO | 2019/126081 A1 | 6/2019 | |
| WO | 2019/126082 A1 | 6/2019 | |
| WO | 2019/126083 A1 | 6/2019 | |
| WO | 2019/126113 A1 | 6/2019 | |
| WO | 2019/126242 A1 | 6/2019 | |
| WO | 2019/126253 A1 | 6/2019 | |
| WO | 2019/220390 A1 | 11/2019 | |
| WO | 2019/238616 A1 | 12/2019 | |
| WO | 2019/238629 A1 | 12/2019 | |

OTHER PUBLICATIONS

Alper, P., et al., "Discovery of potent, orally bioavailable in vivo efficacious antagonists of the TLR7/8 pathway" Bioorg Med Chem Lett 30(17):127366 (1-5) (Sep. 1, 2020).
International Preliminary Report on Patentability for PCT/EP2019/069609 dated Jan. 26, 2021.
International Search Report for PCT/EP2019/069609 dated Sep. 23, 2019.
Knoepfel, T., et al., "Target-Based Identification and Optimization of 5-Indazol-5-yl Pyridones as Toll-like Receptor 7 and 8 Antagonists Using a Biochemical TLR8 Antagonist Competition Assay" J Med Chem 63(15):8276-8295 (Jul. 30, 2020).
Muci and Buchwald et al., "Practical Palladium Catalysts for C—N and C—O Bond Formation" Topics in Current Chemistry 219:131-209 ( 2002).
Mussari, C., et al., "Discovery of Potent and Orally Bioavailable Small Molecule Antagonists of Toll-like Receptors 7/8/9 (TLR7/8/9)" ACS Med Chem Lett 11(9):1751-1758 (Jul. 29, 2020).
Ruiz-Castillo, P., et al., "Applications of Palladium-Catalyzed C—N Cross-Coupling Reactions" ACS Chem Rev 116(19):12564-12649 (Sep. 30, 2016).
Wolfe, J et al., "Rational Development of Practical Catalysts for Aromatic Carbon - Nitrogen Bond Formation" ACC Chem Res 31(12):805-818 (Oct. 21, 1998).

* cited by examiner

*Primary Examiner* — Bahar Craigo
*Assistant Examiner* — Manahil Mirghani Ali Abdalhameed
(74) *Attorney, Agent, or Firm* — Genentech, Inc.

(57) ABSTRACT

The present invention relates to compounds of formula (I), wherein $R^1$ to $R^4$ are as described herein, and their pharmaceutically acceptable salt, enantiomer or diastereomer thereof, and compositions including the compounds and methods of using the compounds.

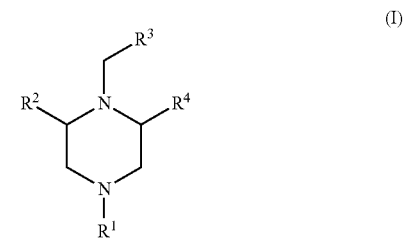

(I)

14 Claims, No Drawings

PIPERAZINE COMPOUNDS FOR THE TREATMENT OF AUTOIMMUNE DISEASE

The present invention relates to organic compounds useful for therapy and/or prophylaxis in a mammal, and in particular to antagonist of TLR7 and/or TLR8 and/or TLR9 useful for treating systemic lupus erythematosus or lupus nephritis.

FIELD OF THE INVENTION

Autoimmune connective tissue disease (CTD) include prototypical autoimmune syndromes such as Systemic Lupus Erythematosus (SLE), primary Sjögren's syndrome (pSjS), mixed connective tissue disease (MCTD), Dermatomyositis/Polymyositis (DM/PM), Rheumatoid Arthritis (RA), and systemic sclerosis (SSc). With the exception of RA, no really effective and safe therapies are available to patients. SLE represents the prototypical CTD with a prevalence of 20-150 per 100,000 and causes broad inflammation and tissue damage in distinct organs, from commonly observed symptoms in the skin and joints to renal, lung, or heart failure. Traditionally, SLE has been treated with non-specific anti-inflammatory or immunosuppressive drugs. However, long term usage of immunosuppressive drug, e.g. corticosteroids is only partially effective, and is associated with undesirable toxicity and side effects. Belimumab is the only FDA-approved drug for lupus in the last 50 years, despite its modest and delayed efficacy in only a fraction of SLE patients (Navarra, S. V. et al Lancet 2011, 377, 721.). Other biologics, such as anti-CD20 mAbs, mAbs against or soluble receptors of specific cytokines, have failed in most clinical studies. Thus, novel therapies are required that provide sustained improvement in a greater proportion of patient groups and are safer for chronic use in many autoimmune as well as auto-inflammation diseases.

Toll Like Receptors (TLR) are an important family of pattern recognition receptors (PRR) which can initiate broad immune responses in a wide variety of immune cells. As natural host defense sensors, endosomal TLRs 7, 8 and 9 recognize nucleic acids derived from viruses, bacteria; specifically, TLR7/8 and TLR9 recognize single-stranded RNA (ssRNA) and single-stranded CpG-DNA, respectively. However, aberrant nucleic acid sensing of TRL7,8,9 is considered as a key node in a broad of autoimmune and auto-inflammatory diseases (Krieg, A. M. et al. Immunol. Rev. 2007, 220, 251. Jimenez-Dalmaroni, M. J. et al Autoimmun Rev. 2016, 15, 1. Chen, J. Q., et al. Clinical Reviews in Allergy & Immunology 2016, 50, 1.). Anti-RNA and anti-DNA antibodies are well established diagnostic markers of SLE, and these antibodies can deliver both self-RNA and self-DNA to endosomes. While self-RNA complexes can be recognized by TLR7 and TLR8, self-DNA complexes can trigger TLR9 activation. Indeed, defective clearance of self-RNA and self-DNA from blood and/or tissues is evident in SLE (Systemic Lupus Erythematosus) patients. TLR7 and TLR9 have been reported to be upregulated in SLE tissues, and correlate with chronicity and activity of lupus nephritis, respectively. In B cells of SLE patients, TLR7 expression correlates with anti-RNP antibody production, while TLR9 expression with IL-6 and anti-dsDNA antibody levels. Consistently, in lupus mouse models, TLR7 is required for anti-RNA antibodies, and TLR9 is required for anti-nucleosome antibody. On the other hand, overexpression of TLR7 or human TLR8 in mice promotes autoimmunity and auto-inflammation. Moreover, activation of TLR8 specifically contributes to inflammatory cytokine secretion of mDC/ macrophages, neutrophil NETosis, induction of Th17 cells, and suppression of Treg cells. In addition to the described role of TLR9 in promoting autoantibody production of B cells, activation of TLR9 by self-DNA in pDC also leads to induction of type I IFNs and other inflammatory cytokines. Given these roles of TLR9 in both pDC and B cells, both as key contributors to the pathogenesis of autoimmune diseases, and the extensive presence of self-DNA complexes that could readily activate TLR9 in many patients with autoimmune diseases, it may have extra benefit to further block self-DNA mediated TLR9 pathways on top of inhibition of TLR7 and TLR8 pathways. Taken together, TLR7, 8, and 9 pathways represent new therapeutic targets for the treatment of autoimmune and auto-inflammatory diseases, for which no effective steroid-free and non-cytotoxic oral drugs exist, and inhibition of all these pathways from the very upstream may deliver satisfying therapeutic effects. As such, we invented oral compounds that target and suppress TLR7, TLR8 and TLR9 for the treatment of autoimmune and auto-inflammatory diseases.

SUMMARY OF THE INVENTION

The present invention relates to novel compounds of formula (I),

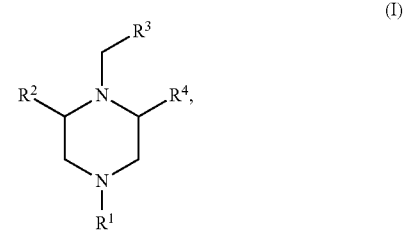

wherein
$R^1$ is

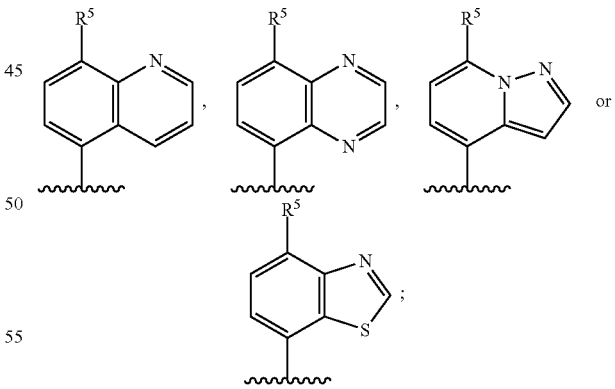

wherein $R^5$ is cyano, $C_{1-6}$alkoxy, $C_{1-6}$alkyl or halogen;
$R^2$ is $C_{1-6}$alkyl;
$R^3$ is $R^{3a}$ or $-COR^{3b}$; wherein
  $R^{3a}$ is phenyl substituted by piperazinyl and (hydroxy$C_{1-6}$alkyl)piperazinyl;
    pyridinyl substituted by piperazinyl, $C_{1-6}$alkylpiperazinyl, 9-oxa-3,7-diazabicyclo[3.3.1]nonanyl, (halopyrrolidinyl)amino, (pyrrolidinylcarbonyl)piperazinyl or (((C$_{1-6}$alkyl)2amino)$C_{1-6}$alkylcarbonyl)piperazinyl; or pyrimidinyl substituted by piperazinyl or (((C$_{1-6}$alkyl)2amino)C$_{1-6}$alkylcarbonyl)piperazinyl;

R$^{3b}$ is 7,8-dihydro-5H-1,6-naphthyridinyl substituted by piperazinyl;
3,4-dihydro-1H-isoquinolinyl substituted by piperazinyl;
isoindolinyl substituted by piperazinyl;
phenylamino substituted by piperazinyl;
1,2,3,4-tetrahydroisoquinolinyl; or
C$_{1-6}$alkylpiperidinylpiperidinyl;

R$^{4}$ is C$_{1-6}$alkyl or H;
or a pharmaceutically acceptable salt, enantiomer or diastereomer thereof.

Another object of the present invention is related to novel compounds of formula (I), their manufacture, medicaments based on a compound in accordance with the invention and their production as well as the use of compounds of formula (I) as TLR7 and/or TLR8 and/or TLR9 antagonist, and for the treatment or prophylaxis of systemic lupus erythematosus or lupus nephritis. The compounds of formula (I) show superior TLR7 and/or TLR8 and/or TLR9 antagonism activity. In addition, the compounds of formula (I) also show good hPBMC, cytotoxicity, solubility, human microsome stability and SDPK profiles, as well as low CYP inhibition.

DETAILED DESCRIPTION OF THE INVENTION

Definitions

The term "C$_{1-6}$alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "C$_{1-6}$alkyl" groups are methyl, ethyl and n-propyl.

The term "C$_{1-6}$alkoxy" denotes C$_{1-6}$alkyl-O—.

The term "halogen" and "halo" are used interchangeably herein and denote fluoro, chloro, bromo, or iodo.

The term "halopyrrolidinyl" denotes a pyrrolidinyl group wherein at least one of the hydrogen atoms of the pyrrolidinyl group has been replaced by same or different halogen atoms, particularly fluoro atoms. Examples of halopyrrolidinyl include fluoropyrrolidinyl, difluoropyrrolidinyl or trifluoropyrrolidinyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "A pharmaceutically active metabolite" denotes a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

Antagonist of TLR7 and/or TLR8 and/or TLR9

The present invention relates to a compound of formula (I),
wherein

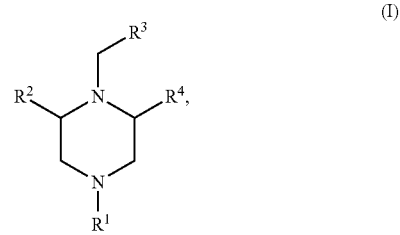

R¹ is

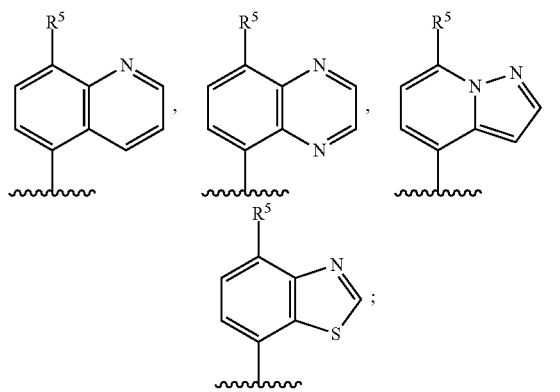

wherein R⁵ is cyano, $C_{1-6}$alkoxy, $C_{1-6}$alkyl or halogen;
R² is $C_{1-6}$alkyl;
R³ is $R^{3a}$ or —$COR^{3b}$; wherein
 $R^{3a}$ a is phenyl substituted by piperazinyl and (hydroxy$C_{1-6}$alkyl)piperazinyl;
  pyridinyl substituted by piperazinyl, $C_{1-6}$alkylpiperazinyl, 9-oxa-3,7-diazabicyclo[3.3.1]nonanyl, (halopyrrolidinyl)amino, (pyrrolidinylcarbonyl)piperazinyl or ((($C_{1-6}$alkyl)2amino)$C_{1-6}$alkylcarbonyl)piperazinyl; or
  pyrimidinyl substituted by piperazinyl or ((($C_{1-6}$alkyl)2amino)$C_{1-6}$alkylcarbonyl)piperazinyl;
 $R^{3b}$ is 7,8-dihydro-5H-1,6-naphthyridinyl substituted by piperazinyl;
  3,4-dihydro-1H-isoquinolinyl substituted by piperazinyl;
  isoindolinyl substituted by piperazinyl;
  phenylamino substituted by piperazinyl;
  1,2,3,4-tetrahydroisoquinolinyl; or
  $C_{1-6}$alkylpiperidinylpiperidinyl;
R⁴ is $C_{1-6}$alkyl or H;
or a pharmaceutically acceptable salt, enantiomer or diastereomer thereof.

Another embodiment of present invention is (ii) a compound of formula (I),
wherein

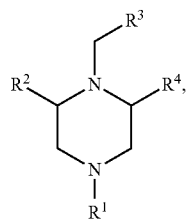
(I)

R¹ is

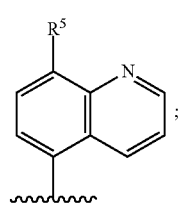

wherein R⁵ is cyano;
R² is $C_{1-6}$alkyl;
R³ is $R^{3a}$ or —$COR^{3b}$; wherein
 $R^{3a}$ is phenyl substituted by piperazinyl and (hydroxy $C_{1-6}$alkyl)piperazinyl;
  pyridinyl substituted by piperazinyl, $C_{1-6}$alkylpiperazinyl, 9-oxa-3,7-diazabicyclo[3.3.1]nonanyl, (halopyrrolidinyl)amino, (pyrrolidinylcarbonyl)piperazinyl or ((($C_{1-6}$alkyl)$_2$amino)$C_{1-6}$alkylcarbonyl)piperazinyl; or
  pyrimidinyl substituted by piperazinyl or ((($C_{1-6}$alkyl)$_2$amino)$C_{1-6}$alkylcarbonyl)piperazinyl;
 $R^{3b}$ is 7,8-dihydro-5H-1,6-naphthyridinyl substituted by piperazinyl;
  3,4-dihydro-1H-isoquinolinyl substituted by piperazinyl;
  isoindolinyl substituted by piperazinyl;
  phenylamino substituted by piperazinyl;
  1,2,3,4-tetrahydroisoquinolinyl; or
  $C_{1-6}$alkylpiperidinylpiperidinyl;
R⁴ is $C_{1-6}$alkyl or H;
or a pharmaceutically acceptable salt, enantiomer or diastereomer thereof.

A further embodiment of present invention is (iii) a compound of formula (I) according to (i) or (ii), wherein R¹ is

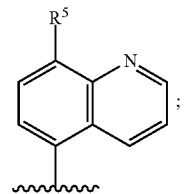

wherein R⁵ is cyano;
R² is methyl;
R³ is $R^{3a}$ or —$COR^{3b}$; wherein
 $R^{3a}$ is piperazinylphenyl; (hydroxymethyl)piperazinylphenyl; piperazinylpyridinyl; (methylpiperazinyl)pyridinyl; 9-oxa-3,7-diazabicyclo[3.3.1]nonanylpyridinyl; ((fluoropyrrolidinyl)amino)pyridinyl; ((pyrrolidinylcarbonyl)piperazinyl)pyridinyl; (((dimethylamino)acetyl)piperazinyl)pyridinyl; piperazinylpyrimidinyl; or ((dimethylamino)acetyl)piperazinylpyrimidinyl;
 $R^{3b}$ is piperazinyl-7,8-dihydro-5H-1,6-naphthyridinyl; piperazinyl-3,4-dihydro-1H-isoquinolinyl; piperazinylisoindolinyl; piperazinylphenylamino; 1,2,3,4-tetrahydroisoquinolinyl; or methylpiperidinylpiperidinyl;
R⁴ is methyl or H;
or a pharmaceutically acceptable salt, enantiomer or diastereomer thereof.

A further embodiment of present invention is (iv) a compound of formula (I) according to any one of (i) to (iv), wherein R³ is $R^{3a}$ or —$COR^{3b}$; wherein $R^{3a}$ is pyridinyl substituted by piperazinyl; $R^{3b}$ is isoindolinyl substituted by piperazinyl.

Another embodiment of present invention is that (v) compounds of formula (I) are selected from the following:
 5-[(3R,5S)-3,5-Dimethyl-4-[(4-piperazin-1-ylphenyl)methyl]piperazin-1-yl]quinoline-8-carbonitrile;
 5-[(3R,5R)-3,5-Dimethyl-4-[(4-piperazin-1-ylphenyl)methyl]piperazin-1-yl]quinoline-8-carbonitrile;
 5-[(3R,5S)-3,5-Dimethyl-4-[(6-piperazin-1-yl-3-pyridyl)methyl]piperazin-1-yl]quinoline-8-carbonitrile;
 5-[(3S,5R)-3,5-Dimethyl-4-[(5-piperazin-1-ylpyrimidin-2-yl)methyl]piperazin-1-yl]quinoline-8-carbonitrile;

5-[(3S,5R)-3,5-Dimethyl-4-[(5-piperazin-1-yl-2-pyridyl)methyl]piperazin-1-yl]quinoline-8-carbonitrile;

5-[(3S,5R)-4[[5-[-4-[2-(Dimethylamino)acetyl]piperazin-1-yl]pyrimidin-2-yl]methyl]-3-5-dimethyl-piperazin-1-yl]quinoline-8-carbonitrile;

5-[(3S,5R)-3,5-dimethyl-4-[[5-(4-methylpiperazin-1-yl)-2-pyridyl]methyl]piperazin-1-yl]quinoline-8-carbonitrile;

5-[(3S,5R)-3,5-Dimethyl-4-[[5-(9-oxa-3,7-diazabicyclo[3.3.1]nonan-3-yl)-2-pyridyl]methyl]piperazin-1-yl]quinoline-8-carbonitrile;

5-[(3R,5S)-3,5-Dimethyl-4-[[5-[[(3R,4S)-4-fluoropyrrolidin-3-yl]amino]-2-pyridyl]methyl]piperazin-1-yl]quinoline-8-carbonitrile;

5-[(3R,5S)-3,5-Dimethyl-4-[[5-[4-(pyrrolidine-2-carbonyl)piperazin-1-yl]-2-pyridyl]methyl]piperazin-1-yl]quinoline-8-carbonitrile;

5-[(3S,5R)-4-[[5-[4-[2-(Dimethylamino)acetyl]piperazin-1-yl]-2-pyridyl]methyl]-3,5-dimethyl-piperazin-1-yl]quinoline-8-carbonitrile;

5-[(3R,5S)-4-[[4-[2-(Hydroxymethyl)piperazin-1-yl]phenyl]methyl]-3,5-dimethyl-piperazin-1-yl]quinoline-8-carbonitrile;

5-[(3R,5S)-3,5-Dimethyl-4-[2-oxo-2-(2-piperazin-1-yl-7,8-dihydro-5H-1,6-naphthyridin-6-yl)ethyl]piperazin-1-yl]quinoline-8-carbonitrile;

5-[(3R,5S)-3,5-Dimethyl-4-[2-oxo-2-(6-piperazin-1-yl-3,4-dihydro-1H-isoquinolin-2-yl)ethyl]piperazin-1-yl]quinoline-8-carbonitrile;

5-[(3R,5S)-3,5-Dimethyl-4-[2-oxo-2-(7-piperazin-1-yl-3,4-dihydrp-1H-isoquinolin-2-yl)ethyl]piperazin-1-yl]quinoline-8-carbonitrile;

5-[(3R,5S)-3,5-Dimethyl-4-[2-oxo-2-(5-piperazin-1-ylisoindolin-2-yl)ethyl]piperazin-1-yl]quinoline-8-carbonitrile;

2-[4-(8-Cyano-5-quinolyl)-2-methyl-piperazin-1-yl]-N-(4-piperazin-1-ylphenyl)acetamide;

2-[4-(8-Cyano-5-quinolyl)-2-methyl-piperazin-1-yl]-N-(1,2,3,4-tetrahydroisoquinolin-6-yl)acetamide; and 5-[3-methyl-4-[2-[4-(1-methyl-4-piperidyl)-1-piperidyl]-2-oxo-ethyl]piperazin-1-yl]quinoline-8-carbonitrile;

or a pharmaceutically acceptable salt, enantiomer or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^6$ are as defined above unless otherwise indicated. Furthermore, and unless explicitly otherwise stated, all reactions, reaction conditions, abbreviations and symbols have the meanings well known to a person of ordinary skill in organic chemistry.

A general synthetic route for preparing the compound of formula (I) is shown in Scheme 1 below.

Scheme 1

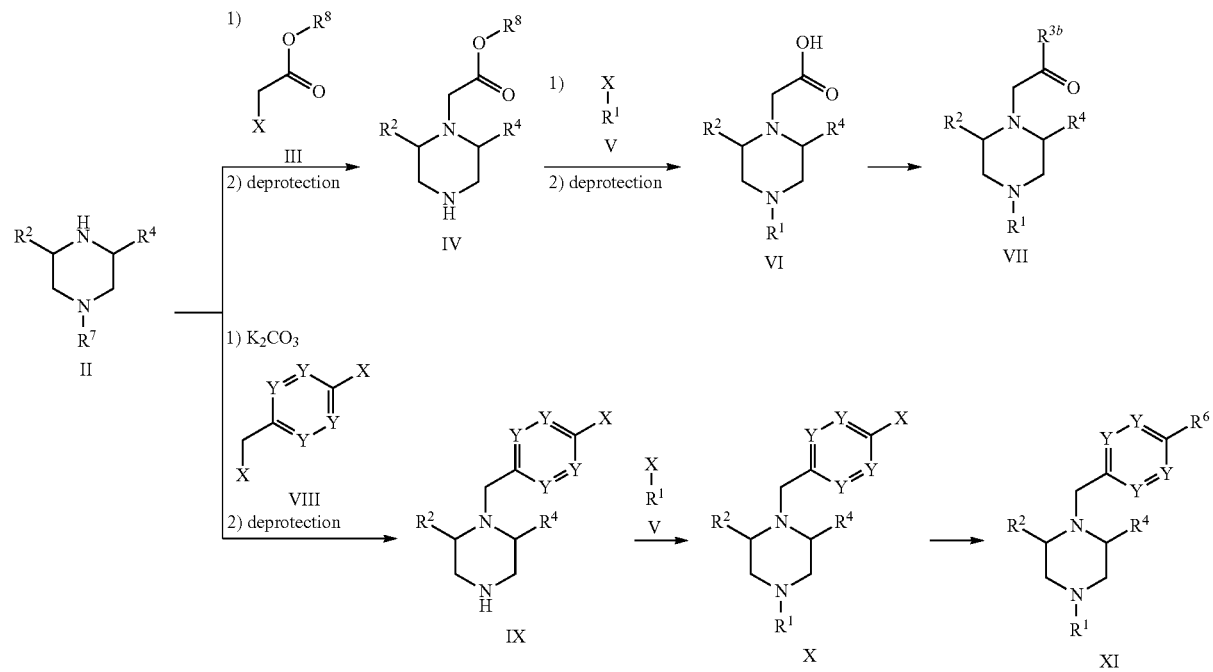

wherein X is halogen or leaving group, for example, OTf or OMs; Y is N or CH; $R^6$ is primary or secondary amine including linear and cyclic amines, such as piperazine; $R^7$ and $R^8$ are protecting groups, for example, $R^7$ is Boc and $R^8$ is benzyl.

Alkylating of protected amine (II) by a-halo ester (III) under basic conditions, followed by selective removal of protecting group $R^7$, can afford free amine (IV). Conversion of carboxylic acid (VI) from free amine (IV) can be achieved by nucleophilic aromatic substitution conditions (e.g. heating with aryl halide (V) in the presence of DIEPA in DMSO), or Buchwald-Hartwig amination conditions (e.g.

heating with halide (V) in the presence of a catalyst, such as Ruphos Pd-G2, and a base, such as Cs$_2$CO$_3$), followed by removal of protecting group R$^8$. Treatment of carboxylic acid (VI) with amine HR$^{3b}$, in the presence of a coupling reagent, such as HATU, and base, such as DIPEA, can afford amide (VII).

Alternatively, protected amine (II) can be alkylated by halide (VIII), followed by removal of protecting group R$^7$. The resultant free amine (IX) can be used to react with aryl halide (V) under nucleophilic aromatic substitution conditions (e.g. heating with aryl halide (V) in the presence of DIEPA in DMSO), to afford intermediate (X). Compound of formula (X) can be used as a common intermediate for further functionalization under metal catalyzed coupling conditions, such as Buchwald-Hartwig amination, Suzuki coupling, Negishi coupling, Stille coupling, or Pd-catalyzed C=O insertion. For example, under Buchwald-Hartwig amination conditions (ref: *Acc. Chem. Res.* 1998, 31, 805-818; *Chem. Rev.* 2016, 116, 12564-12649; *Topics in Current Chemistry*, 2002, 219, 131-209; and references cited therein), compound of formula (XI) can be generated from compound of formula (X) in the presence of an amine HR$^6$, and a catalyst, such as Ruphos Pd-G2, and a base, such as Cs$_2$CO$_3$.

used to react with amine HR$^{3b}$ in the presence of a coupling reagent, such as HATU, and base, such as DIPEA, to afford amide (VII).

Alternatively, alkylating of amine (XIII) by halide (VIII) under basic conditions, followed by removal of protecting group R$^8$, can afford aryl halide (X), which can be used as a common intermediate for further functionalization under metal catalyzed coupling conditions, such as Buchwald-Hartwig amination, Suzuki coupling, Negishi coupling, Stille coupling, or Pd-catalyzed C=O insertion. For example, under Buchwald-Hartwig amination conditions (ref: *Acc. Chem. Res.* 1998, 31, 805-818; *Chem. Rev.* 2016, 116, 12564-12649; *Topics in Current Chemistry*, 2002, 219, 131-209; and references cited therein), compound of formula (XI) can be generated from compound of formula (X) in the presence of an amine HR$^6$, and a catalyst, such as Ruphos Pd-G2, and a base, such as Cs$_2$CO$_3$.

Compounds of this invention can be obtained as mixtures of diastereomers or enantiomers, which can be separated by methods well known in the art, e.g. (chiral) HPLC or SFC.

This invention also relates to a process for the preparation of a compound of formula (I) comprising any of the following steps:

Scheme 2

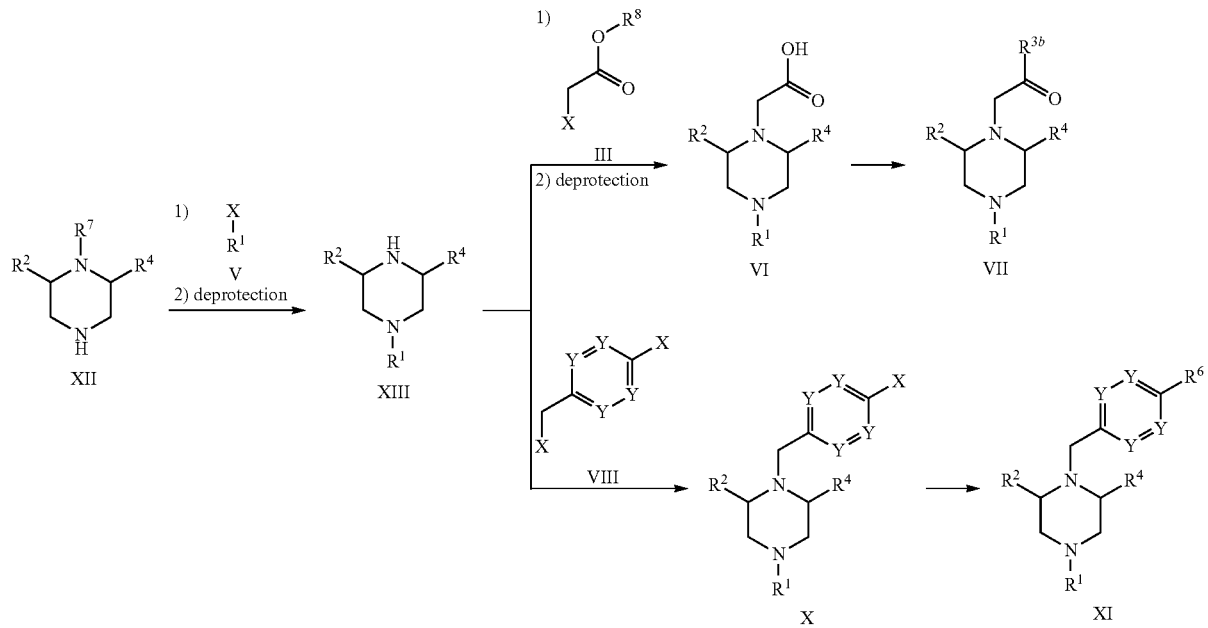

wherein X is halogen or leaving group, for example, OTf or OMs; Y is N or CH; R$^6$ is primary or secondary amine including linear and cyclic amines, such as piperazine; R$^7$ and R$^8$ are protecting groups, for example, R$^7$ is Boc and R$^8$ is benzyl.

In another synthetic route (Scheme 2), common intermediate (XIII) can be afforded by reacting protected amine (XII) with aryl halide (V) under nucleophilic aromatic substitution conditions (e.g. heating with aryl halide (V) in the presence of DIEPA in DMSO), or Buchwald-Hartwig amination conditions (e.g. heating with halide (V) in the presence of a catalyst, such as Ruphos Pd-G2, and a base, such as Cs$_2$CO$_3$), followed by removal of protecting group R$^7$. Alkylating of amine (XIII) by α-halo ester (III) under basic conditions, followed by selective removal of protecting group R$^8$, can afford carboxylic acid (VI), which can be a) the coupling reaction of compound of formula (VI),

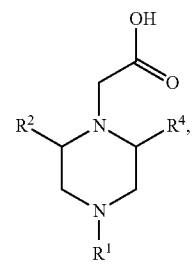

and an amine HR[3b] in the presence of a coupling reagent and a base;

b) the Buchwald-Hartwig amination reaction of compound of formula (X),

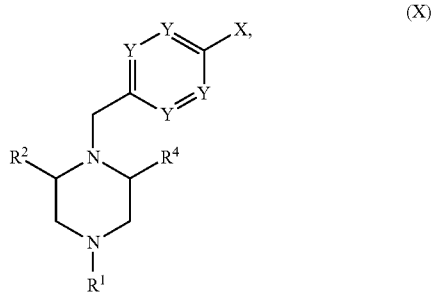

and an amine HR[6] in the presence of a catalyst and a base; wherein, in step a), the coupling reagent can be, for example, HATU; and base can be, for example, DIPEA;

in step b), the catalyst can be, for example, Ruphos Pd-G2; the base can be, for example, $Cs_2CO_3$.

A compound of formula (I) when manufactured according to the above process with achiral or chiral starting materials is also an object of the invention.

Indications and Methods of Treatment

The present invention provides compounds that can be used as TLR7 and/or TLR8 and/or TLR9 antagonist, which inhibits pathway activation through TLR7 and/or TLR8 and/or TLR9 as well as respective downstream biological events including, but not limited to, innate and adaptive immune responses mediated through the production of all types of cytokines and all forms of auto-antibodies. Accordingly, the compounds of the invention are useful for blocking TLR7 and/or TLR8 and/or TLR9 in all types of cells that express such receptor(s) including, but not limited to, plasmacytoid dendritic cell, B cell, T cell, macrophage, monocyte, neutrophil, keratinocyte, epithelial cell. As such, the compounds can be used as a therapeutic or prophylactic agent for systemic lupus erythematosus and lupus nephritis.

The present invention provides methods for treatment or prophylaxis of systemic lupus erythematosus and lupus nephritis in a patient in need thereof.

Another embodiment includes a method of treating or preventing systemic lupus erythematosus and lupus nephritis in a mammal in need of such treatment, wherein the method comprises administering to said mammal a therapeutically effective amount of a compound of formula (I), a stereoisomer, tautomer, prodrug or pharmaceutically acceptable salt thereof.

EXAMPLES

The invention will be more fully understood by reference to the following examples. They should not, however, be construed as limiting the scope of the invention.

Abbreviations

The invention will be more fully understood by reference to the following examples. They should not, however, be construed as limiting the scope of the invention.

Abbreviations used herein are as follows:
ACN: acetonitrile
$Boc_2O$: di-tert-butyl dicarbonate
$Tf_2O$: triflic anhydride
DCM: dichloromethane
DDI drug-drug-interaction
DIPEA diethylisopropylamine
DMA dimethylacetamide
EA or EtOAc: ethyl acetate
FA: formic acid
HATU 1-[Bis(dimethylamino)methylene]-1H-1,2,3-triazolo[4,5-b]pyridinium 3-oxid hexafluorophosphate
HLM human liver micro some
hr hour
hrs hours
$IC_{50}$: half inhibition concentration
LCMS liquid chromatography-mass spectrometry
LYSA lyophilisation solubility assay
MS: mass spectrometry
PE: petroleum ether
prep-HPLC: preparative high performance liquid chromatography
rt: rt
RT: retention time
RuPhos Pd G2: chloro(2-dicyclohexylphosphino-2',6'-diisopropoxy-1,1'-biphenyl)[2-(2'-amino-1,1'-biphenyl)]palladium(II) 2nd generation
SFC: supercritical fluid chromatography
TFA: trifluoroacetic acid
v/v volume ratio General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 μm, OBDTM 30×100 mm) column, SunFire™ Prep-C18 (5 μm, OBD™ 30×100 mm) column, Phenomenex Synergi-C18 (10 μm, 25×150 mm) or Phenomenex Gemini-C18 (10 μm, 25×150 mm). Waters AutoP purification System (Sample Manager 2767, Pump 2525, Detector: Micromass ZQ and UV 2487, solvent system: acetonitrile and 0.1% ammonium hydroxide in water; acetonitrile and 0.1% FA in water or acetonitrile and 0.1% TFA in water). Or Gilson-281 purification System (Pump 322, Detector: UV 156, solvent system: acetonitrile and 0.05% ammonium hydroxide in water; acetonitrile and 0.225% FA in water; acetonitrile and 0.05% HCl in water; acetonitrile and 0.075% TFA in water; or acetonitrile and water).

For SFC chiral separation, intermediates were separated by chiral column (Daicel chiralpak IC, 5 μm, 30×250 mm), AS (10 μm, 30×250 mm) or AD (10 μm, 30×250 mm) using Mettler Toledo Multigram III system SFC, Waters 80Q preparative SFC or Thar 80 preparative SFC, solvent system: $CO_2$ and IPA (0.5% TEA in IPA) or $CO_2$ and MeOH (0.1% $NH_3·H_2O$ in MeOH), back pressure 100 bar, detection UV@254 or 220 nm.

LC/MS spectra of compounds were obtained using a LC/MS (Waters™ Alliance 2795-Micromass ZQ, Shimadzu Alliance 2020-Micromass ZQ or Agilent Alliance 6110-Micromass ZQ), LC/MS conditions were as follows (running time 3 or 1.5 mins):

Acidic condition I: A: 0.1% TFA in $H_2O$; B: 0.1% TFA in acetonitrile;

Acidic condition II: A: 0.0375% TFA in $H_2O$; B: 0.01875% TFA in acetonitrile;

Basic condition I: A: 0.1% $NH_3 H_2O$ in $H_2O$; B: acetonitrile;

Basic condition II: A: 0.025% $NH_3$ $H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(MH)^{+\cdot}$ NMR Spectra were obtained using Bruker Avance 400 MHz.

The microwave assisted reactions were carried out in a Biotage Initiator Sixty microwave synthesizer. All reactions involving air-sensitive reagents were performed under an argon or nitrogen atmosphere. Reagents were used as received from commercial suppliers without further purification unless otherwise noted.

Preparative Examples

The following examples are intended to illustrate the meaning of the present invention but should by no means represent a limitation within the meaning of the present invention:

Example 1

5-[(3R,5S)-3,5-Dimethyl-4-[(4-piperazin-1-ylphenyl)methyl]piperazin-1-yl]quinoline-8-carbonitrile

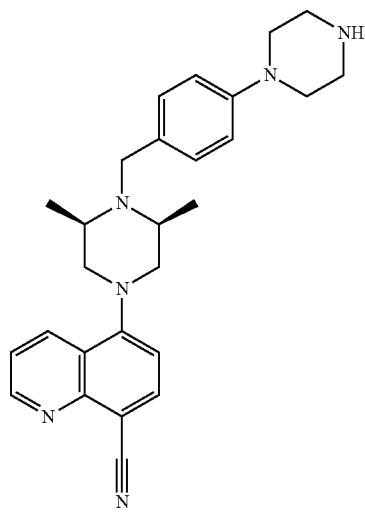 [SMILES: C[C@@H]1CN(c2ccc(C#N)c3ncccc23)C[C@H](C)N1Cc1ccc(N2CCNCC2)cc1]

The title compound was prepared according to the following scheme:

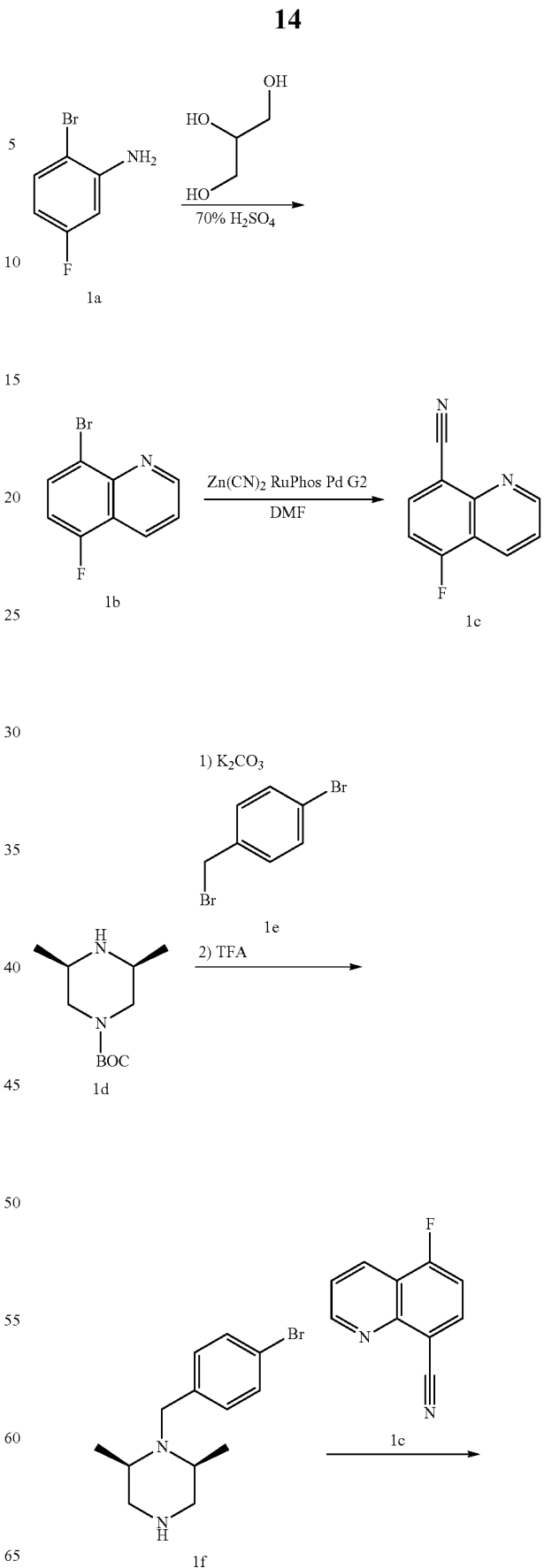

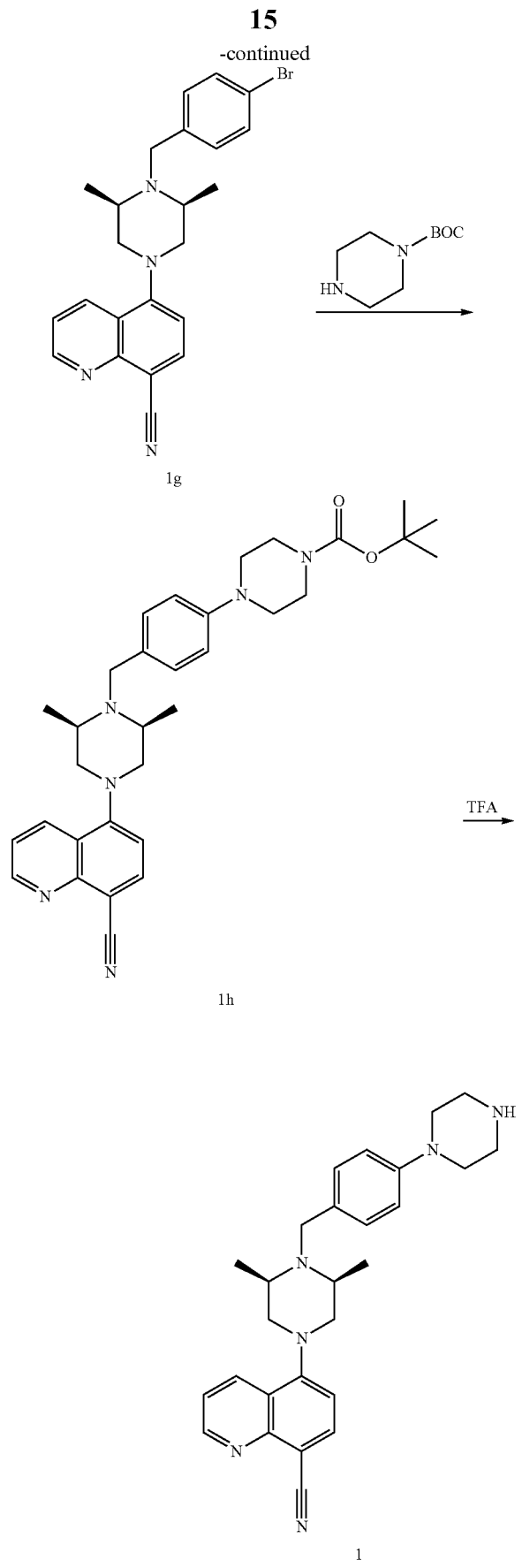

Step 1

Preparation of 8-bromo-5-fluoro-quinoline (Compound 1b)

In a 100 mL flask, 2-bromo-5-fluoroaniline (CAS: 1003-99-2, Accela ChemBio, Catalog: SY020710, 2.0 g, 10.5 mmol), propane-1,2,3-triol (CAS: 56-81-5, Accela ChemBio, Catalog: SY006578, 969 mg, 10.5 mmol) and sodium 3-nitrobenzenesulfonate (CAS: 127-68-4, SigmaAldrich, Catalog: 225193, 2.4 g, 10.5 mmol) were combined with 70% $H_2SO_4$ (20 mL) to afford a dark brown solution, which was heated to 150° C. and stirred for 3 hrs. After being cooled to room temperature, the reaction mixture was poured into ice-water, and neutralized with sodium hydroxide solution. The resultant mixture was filtered. The filter cake was dissolved in EtOAc and filtered again. The resultant filtrate was concentrated in vacuo and the crude material was purified by flash chromatography (silica gel, 40 g, 0% to 30% EtOAc in PE) to afford compound 1b (2.0 g, 84% yield). MS: calc'd 226 and 228 [(M+H)$^+$], measured 226 and 228 [(M+H)$^+$].

Step 2

Preparation of 5-fluoroquinoline-8-carbonitrile (Compound 1c)

To a solution of 8-bromo-5-fluoroquinoline (compound 1b, 4.9 g, 21.7 mmol) in DMF (30 mL) was added dicyanozinc (5.0 g, 43.4 mmol) and RuPhos Pd G2 (CAS: 1375325-68-0, Sigma-Aldrich, Catalog: 753246, 842 mg, 1.1 mmol). The reaction mixture was stirred at 100° C. for 3 hrs, then cooled to room temperature. The reaction mixture was filtered and the filtrate was diluted with water (50 mL), then extracted with EA (80 mL) for three times. The combined organic layer was washed with brine, dried over $Na_2SO_4$, filtered and concentrated in vacuo. The residue was purified by flash chromatography (silica gel, 40 g, 0% to 70% EtOAc in PE) to afford compound 1c (3.0 g, 80% yield). MS: calc'd 173 [(M+H)$^+$], measured 173 [(M+H)$^+$]. $^1$H NMR (400 MHz, METHANOL-$d_4$) δ ppm 9.11 (dd, J=4.28, 1.71 Hz, 1 H), 8.64 (dd, J=8.56, 1.71 Hz, 1 H), 8.29 (dd, J=8.19, 5.62 Hz, 1 H), 7.76 (dd, J=8.56, 4.28 Hz, 1 H), 7.49 (dd, J=9.35, 8.25 Hz, 1 H).

Step 3

Preparation of (2R,6S)-1-[(4-bromophenyl)methyl]-2,6-dimethyl-piperazine (Compound 1f)

To a solution of tert-butyl (3R,5S)-3,5-dimethylpiperazine-1-carboxylate (compound 1d, CAS: 129779-30-2, PharmaBlock, Catalog: PB125871, 100 mg, 467 μmol) and $K_2CO_3$ (129 mg, 933 μmol) in MeCN (5 mL) was added 1-bromo-4-(bromomethyl)benzene (compound 1e, CAS: 589-15-1, Accela ChemBio, Catalog: SY001367, 117 mg, 467 μmol). The resultant mixture was heated to 80° C. for 14 hrs, then cooled to room temperature. The reaction mixture was filtered and the filter cake was washed with EA (10 mL). The combined filtrate was concentrated in vacuo and purified by flash chromatography (silica gel, 12 g, 10% to 50% EtOAc in PE).

The purified intermediate was dissolved in DCM (2 mL) and TFA (0.5 mL) was added. The reaction mixture was stirred at room temperature for 3 hrs, then concentrated to afford a crude compound 1f, MS: calc'd 283 and 285 [(M+H)+], measured 283 and 285 [(M+H)+].

Step 4

Preparation of 5-[(3R,5S)-4-[(4-bromophenyl)methyl]-3,5-dimethyl-piperazin-1-yl]quinoline-8-carbonitrile (Compound 1g)

To a solution of 5-fluoroquinoline-8-carbonitrile (compound 1c, 80.9 mg, 470 µmol) in DMSO (2 mL) was added (2R,6S)-1-(4-bromobenzyl)-2,6-dimethylpiperazine (compound 1f, 133 mg, 0.47mmol) and DIEPA (243 mg, 1.88 mmol). The reaction mixture was stirred at 120° C. for 3 hrs, then cooled to room temperature, diluted with water (10 mL), and extracted with EA (15 mL) twice. The combined organic layer was washed with brine, dried over $Na_2SO_4$, filtered and concentrated in vacuo. The residue was purified by flash chromatography (silica gel, 24 g, 10% to 50% EtOAc in PE) to afford compound 1g (150 mg, 73% yield). MS: calc'd 435, 437 [(M+H)+], measured 435, 437 [(M+H)+].

Step 5

Preparation of tert-butyl 4-[4-[[(2R,6S)-4-(8-cyano-5-quinolyl)-2,6-dimethyl-piperazin-1-yl]methyl]phenyl]piperazine-1-carboxylate (Compound 1h)

To a solution of 5-((3R,5S)-4-(4-bromobenzyl)-3,5-dimethylpiperazin-1-yl)quinoline-8-carbonitrile (compound 1g, 45 mg, 103 iumol,) in dioxane (10 mL) was added tert-butyl piperazine-1-carboxylate (CAS: 57260-71-6, Accela ChemBio, Catalog: SY002528, 23.1 mg, 124 µmol), RuPhos Pd G3 (CAS: 1445085-77-7, Sigma-Aldrich, Catalog: 763403; 2.76 mg, 3.1 µmol) and sodium tert-butoxide (30.1 mg, 310 µmol). The reaction mixture was stirred at 80° C. for 14 hrs, then cooled to room temperature, diluted with water (20 mL), and extracted with EA (20 mL) twice. The combined organic layer was washed with brine, dried over $Na_2SO_4$, filtered and concentrated in vacuo. The residue was purified by flash chromatography (silica gel, 40 g, 20% to 100% EtOAc in PE) to afford compound 1h (35 mg, 62% yield). MS: calc'd 541 [(M+H)+], measured 541 [(M+H)+].

Step 6

Preparation of 5-[(3R,5S)-3,5-dimethyl-4-[(4-piperazin-1-ylphenyl) methyl]piperazin-1-yl]quinoline-8-carbonitrile (Example 1)

To a solution of tert-butyl 4-[4-[[(2R,6S)-4-(8-cyano-5-quinolyl)-2,6-dimethyl-piperazin-1-yl]methyl]phenyl]piperazine-1-carboxylate (compound 1h) (20 mg, 37 µmol) in DCM (2 mL) was added TFA (0.5 mL). The reaction mixture was stirred at room temperature for 3 hrs, then concentrated to afford a crude product, which was purified by prep-HPLC to afford Example 1 (5 mg, 30%). MS: calc'd 441 [(M+H)+], measured 441 [(M+H)+]. $^1$H NMR (400 MHz, METHANOL-$d_4$) δ ppm 8.84 (dd, J=4.2, 1.7 Hz, 1H), 8.40 (dd, J=8.6, 1.5 Hz, 1H), 8.01 (d, J=7.9 Hz, 1H), 7.48 (dd, J=8.6, 4.3 Hz, 1H), 7.24 (d, J=8.7 Hz, 2H), 7.09 (d, J=8.1 Hz, 1H), 6.88 (d, J=8.7 Hz, 2H), 4.49 (br s, 2H), 3.88 (s, 2H), 3.01-3.12 (m, 4H), 2.83-2.99 (m, 6H), 2.60-2.72 (m, 2H), 1.14 (d, J=6.1 Hz, 6H).

Example 2

5-[(3R,5R,-3,5-Dimethyl-4-[(4-piperazin-1-ylphenyl)methyl]piperazin-1-yl]quinoline-8-carbonitrile

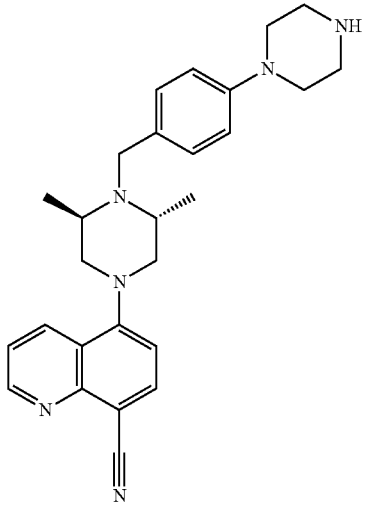 [SMILES: C[C@@H]1CN(c2ccc(C#N)c3ncccc23)C[C@@H](C)N1Cc1ccc(N2CCNCC2)cc1]

The title compound was prepared in analogy to the preparation of Example 1 using (3R,5R)-3,5-dimethylpiperazine-1-carboxylate (CAS: 438049-91-3, PharmaBlock, Catalog: PB05910) instead of (3R,5S)-3,5-dimethylpiperazine-1-carboxylate (compound 1d). Example 2 (12 mg) was obtained. MS: calc'd 441 [(M+H)+], measured 441 [(M+H)+]. $^1$H NMR (400 MHz, METHANOL-$d_4$) δ ppm 8.99 (dd, J=4.3, 1.5 Hz, 1H), 8.71 (dd, J=8.6, 1.5 Hz, 1H), 8.16 (d, J=7.9 Hz, 1H), 7.69 (dd, J=8.6, 4.3 Hz, 1H), 7.57 (d, J=8.7 Hz, 2H), 7.35 (d, J=8.1 Hz, 1H), 7.16 (d, J=8.8 Hz, 2H), 4.80 (br d, J=13.4 Hz, 1H), 4.27 (br d, J=13.4 Hz, 1H), 4.17 (br s, 1H), 3.73 (br d, J=12.5 Hz, 2H), 3.44-3.59 (m, 6H), 3.38-3.44 (m, 4H), 3.15-3.26 (m, 1H), 1.58-1.77 (m, 6H).

Example 3

5-[(3R,5S)-3,5-Dimethyl-4-[(6-piperazin-1-yl-3-pyridyl)methyl]piperazin-1-yl]quinoline-8-carbonitrile

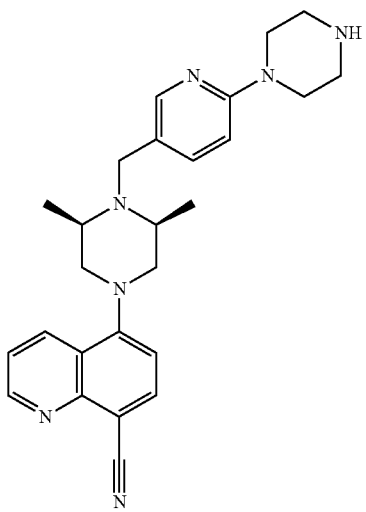 [SMILES: C[C@@H]1CN(c2ccc(C#N)c3ncccc23)C[C@H](C)N1Cc1ccc(N2CCNCC2)nc1]

The title compound was prepared according to the following scheme:

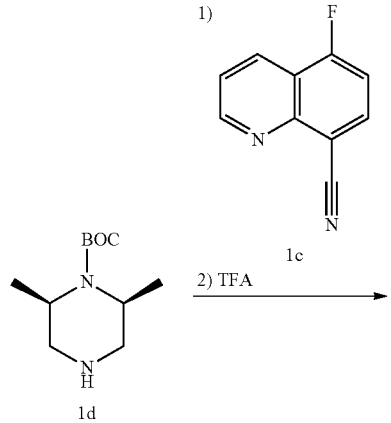

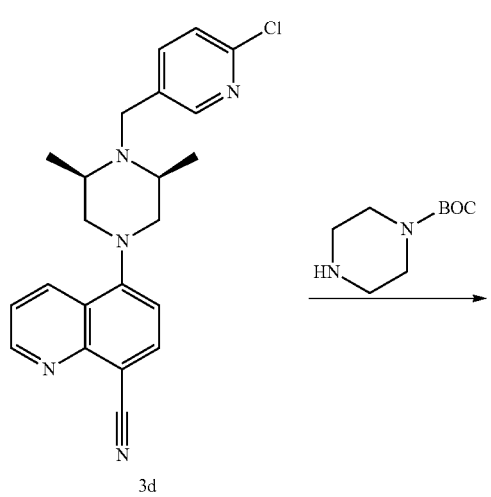

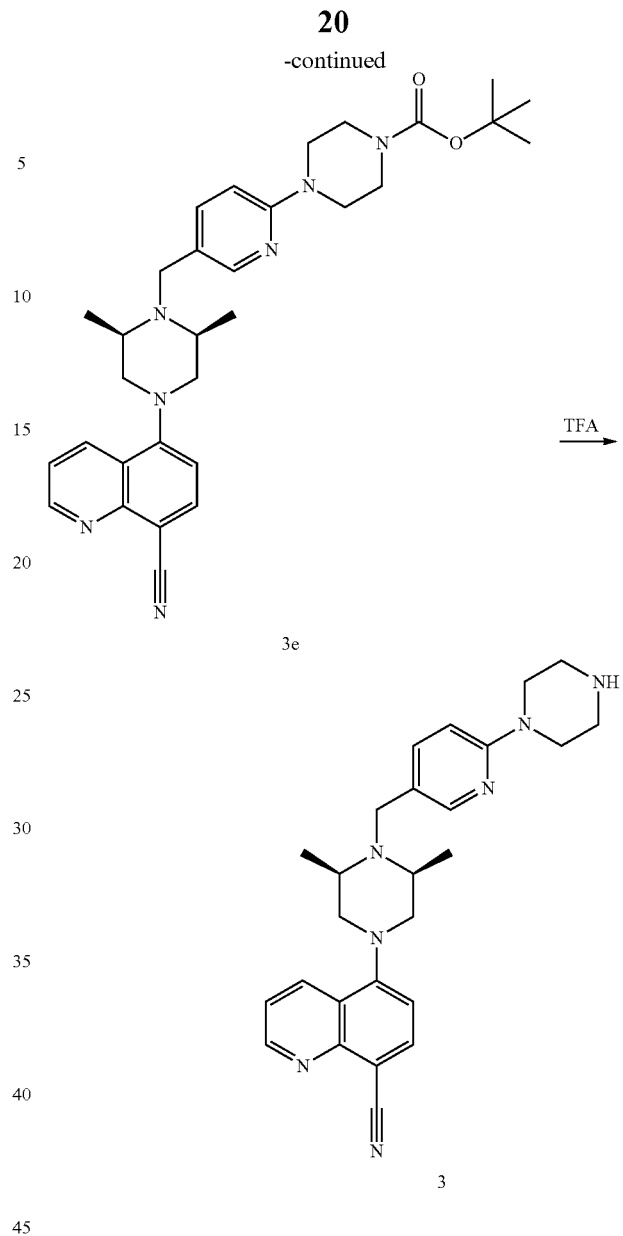

Step 1

Preparation of 5-((3R,5S)-3,5-dimethylpiperazin-1-yl)quinoline-8-carbonitrile (Compound 3b)

To a solution of 5-fluoroquinoline-8-carbonitrile (compound 1, 1.4 g, 8.1 mmol) in DMSO (20 mL) was added (3R,5S)-3,5-dimethylpiperazine-1-carboxylate (compound 1d) (1.7 g, 1.7 mmol) and DIEA (878 mg, 6.8 mmol). The reaction mixture was stirred at 120° C. for 3 hrs, then cooled to room temperature, diluted with water (100 mL), and extracted with EA (150 mL) twice. The combined organic layer was washed with brine, dried over $Na_2SO_4$, filtered and concentrated in vacuo. The residue was purified by flash chromatography (silica gel, 80 g, 10% to 50% EtOAc in PE).

The purified intermediate was dissolved in DCM (20 mL) and TFA (5 mL) was added. The reaction mixture was stirred at room temperature for 3 hrs, then concentrated to afford a crude compound 3b (1.6 g, 75% yield). MS: calc'd 266 [(M+H)$^+$], measured 266 [(M+H)$^+$].

Step 2

Preparation of 5-[(3S,5R)-4-[(6-chloro-3-pyridyl)methyl]-3,5-dimethyl-piperazin-1-yl]quinoline-8-carbonitrile (Compound 3d)

To a solution of 5-((3R,5S)-3,5-dimethylpiperazin-1-yl)quinoline-8-carbonitrile (compound 3b) (95 mg, 357 µmol) and $K_2CO_3$ (98.6 mg, 713 µmol) in MeCN (5 mL) was added 2-chloro-5-(chloromethyl)pyridine (compound 3c, CAS: 70258-18-3, TCI, Catalog: C1628, 90 mg, 556 µmol). The resultant mixture was heated to 80° C. for 14 hrs, then cooled to room temperature. The reaction mixture was filtered and the filter cake was washed with EA (10 mL). The combined filtrate was concentrated in vacuo and purified by flash chromatography (silica gel, 12 g, 10% to 100% EtOAc in PE), to afford compound 3d (110 mg, 79% yield). MS: calc'd 392 [(M+H)$^+$], measured 392 [(M+H)$^+$].

Step 3

Preparation of tert-butyl 4-[5-[[(2R,6S)-4-(8-cyano-5-quinolyl)-2,6-dimethyl-piperazin-1-yl]methyl]-2-pyridyl]piperazine-1-carboxylate (Compound 3e)

To a solution of 5-((3R,5S)-4-((6-chloropyridin-3-yl)methyl)-3,5-dimethylpiperazin-1-y1)quinoline-8-carbonitrile (compound 3d, 55 mg, 140 µmol) in dioxane (10 mL) was added tert-butyl piperazine-1-carboxylate (CAS: 57260-71-6, Accela ChemBio, Catalog: SY002528; 31.4 mg, 168 µmol), RuPhos Pd G2 (CAS: 1375325-68-0, Sigma-Aldrich, Catalog: 753246; 12.2 mg, 14 µmol) and sodium tert-butoxide (9.93 mg, 103 µmol). The reaction mixture was stirred at 80° C. for 14 hrs, then cooled to room temperature, diluted with water (20 mL), and extracted with EA (10 mL) twice. The combined organic layer was washed with brine, dried over $Na_2SO_4$, filtered and concentrated in vacuo. The residue was purified by flash chromatography (silica gel, 12 g, 20% to 100% EtOAc in PE) to afford compound 3e (50 mg, 66% yield). MS: calc'd 542 [(M+H)$^+$], measured 542 [(M+H)$^+$].

Step 4

Preparation of 5-[(3R,5S)-3,5-dimethyl-4-[(6-piperazin-1-yl-3-pyridyl) methyl]piperazin-1-yl]quinoline-8-carbonitrile (Example 3)

To a solution of tert-butyl 4-[5-[[(2R,6S)-4-(8-cyano-5-quinolyl)-2,6-dimethyl-piperazin-1-yl]methyl]-2-pyridyl]piperazine-1-carboxylate (compound 1h) (50 mg, 92 µmol) in DCM (2 mL) was added TFA (0.5 mL). The reaction mixture was stirred at room temperature for 3 hrs, then concentrated to afford a crude product, which was purified by prep-HPLC to afford Example 3 (28 mg, 69%). MS: calc'd 442 [(M+H)$^+$], measured 442 [(M+H)$^+$]. $^1$H NMR (400 MHz, METHANOL-d$_4$) δ ppm 9.01 (dd, J=1.6, 4.3 Hz, 1H), 8.56 (br d, J=7.8 Hz, 1H), 8.47 (s, 1H), 8.20 (d, J=7.9 Hz, 1H), 7.90 (br d, J=8.9 Hz, 1H), 7.64 (dd, J=4.2, 8.5 Hz, 1H), 7.35 (d, J=8.1 Hz, 1H), 7.08 (d, J=8.9 Hz, 1H), 4.71 (br s, 2H), 4.04 -3.86 (m, 4H), 3.69 (br d, J=13.6 Hz, 4H), 3.42 -3.35 (m, 4H), 3.23 -3.06 (m, 2H), 1.68 (d, J=6.2 Hz, 6H).

Example 4

5-[(3S,5R)-3,5-Dimethyl-4-[(5-piperazin-1-ylpyrimidin-2-yl)methyl]piperazin-1-yl]quinoline-8-carbonitrile

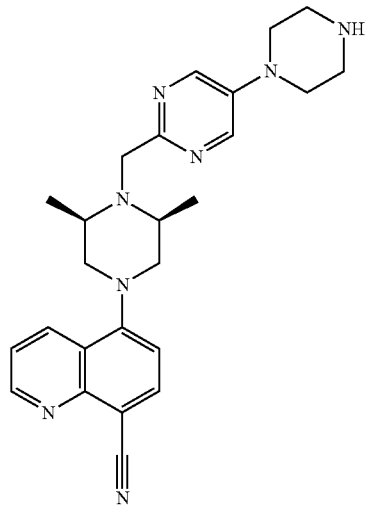 [SMILES: C[C@@H]1CN(c2ccc(C#N)c3ncccc23)C[C@H](C)N1Cc1ncc(N2CCNCC2)cn1]

The title compound was prepared in analogy to the preparation of Example 3 using 5-bromo-2-(bromomethyl)pyrimidine (CAS: 1193116-74-3, BePharm, Catalog: BD266661) instead of 2-chloro-5-(chloromethyl)pyridine (compound 3c). Example 4 (23 mg) was obtained. MS: calc'd 443 [(M+H)$^+$], measured 443 [(M+H)$^+$]. $^1$H NMR (400 MHz, METHANOL-d$_4$) δ ppm 8.91 (dd, J=4.2, 1.7 Hz, 1H), 8.42-8.50 (m, 3H), 8.07 (d, J=8.1 Hz, 1H), 7.55 (dd, J=8.6, 4.3 Hz, 1H), 7.14 (d, J=8.1 Hz, 1H), 4.21 (s, 2H), 3.26-3.36 (m, 7H), 3.17-3.22 (m, 1H), 2.97-3.06 (m, 4H), 2.77 (t, J=11.2 Hz, 2H), 1.30 (d, J=6.2 Hz, 6H).

Example 5

5-[(3S,5R)-3,5-Dimethyl-4-[(5-piperazin-1-yl-2-pyridyl)methyl]piperazin-1-yl]quinoline-8-carbonitrile

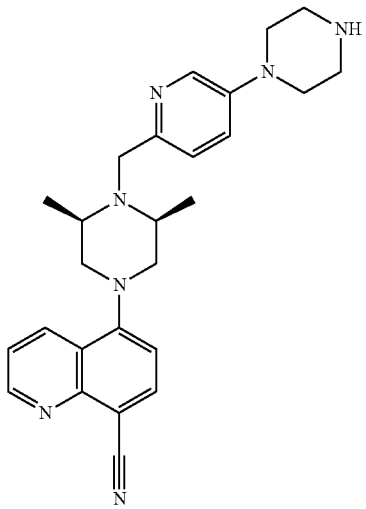 [SMILES: C[C@@H]1CN(c2ccc(C#N)c3ncccc23)C[C@H](C)N1Cc1ccc(N2CCNCC2)cn1]

The title compound was prepared according to the following scheme:

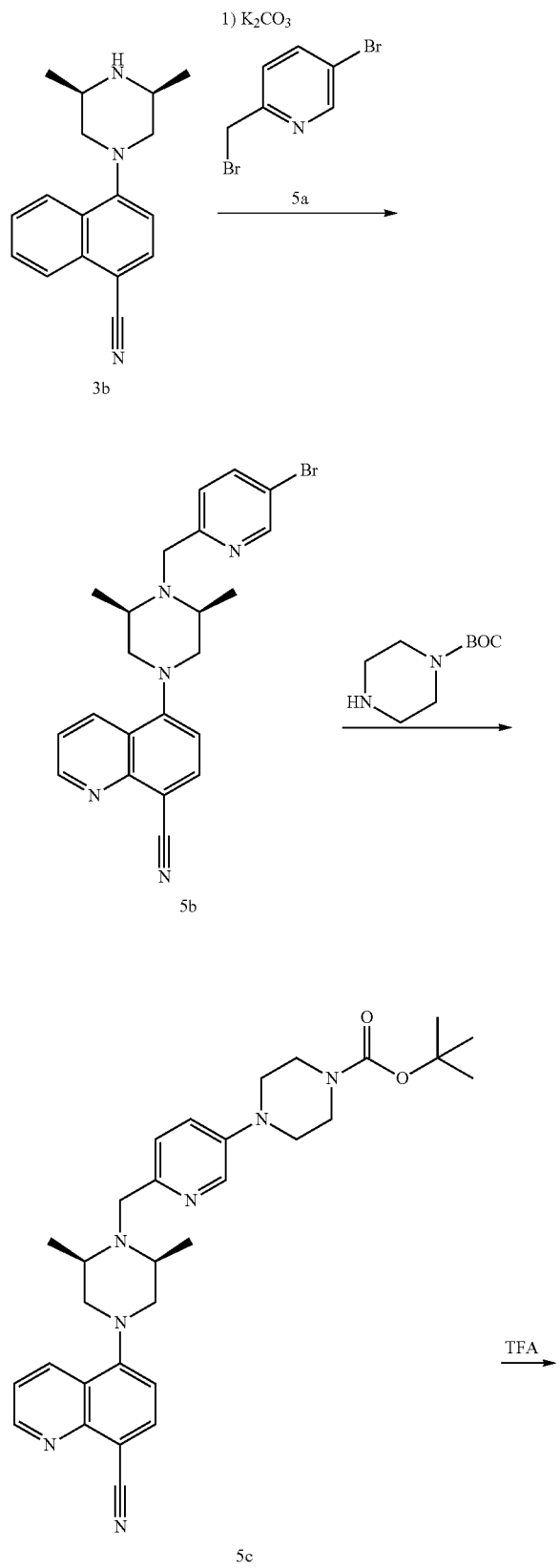 [SMILES: C[C@@H]1CN(c2ccc(C#N)c3ccccc23)C[C@H](C)N1 ; BrCc1ccc(Br)cn1 ; C[C@@H]1CN(c2ccc(C#N)c3ncccc23)C[C@H](C)N1Cc1ccc(Br)cn1 ; CC(C)(C)OC(=O)N1CCNCC1 ; C[C@@H]1CN(c2ccc(C#N)c3ncccc23)C[C@H](C)N1Cc1ccc(N2CCN(C(=O)OC(C)(C)C)CC2)cn1]

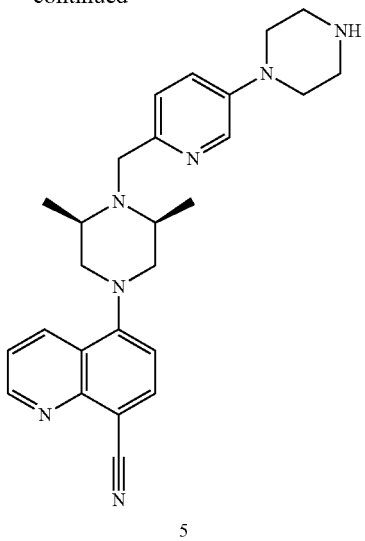

Step 1

Preparation of 5-[(3R,5S)-4-[(5-bromo-2-pyridyl)methyl]-3,5-dimethyl-piperazin-1-yl]quinoline-8-carbonitrile (Compound 5b)

To a solution of 5-((3R,5S)-3,5-dimethylpiperazin-1-yl)quinoline-8-carbonitrile (compound 3b) (95mg, 357 μmol) and $K_2CO_3$ (98.6 mg, 713 μmol) in MeCN (5 mL) was added 5-bromo-2-(bromomethyl)pyridine (compound 5a, CAS: 145218-19-5, Wuxi AppTec, Catalog: LN01365762; 90 mg, 359 μmol). The resultant mixture was heated to 80° C. for 14 hrs, then cooled to room temperature. The reaction mixture was filtered and the filter cake was washed with EA (10 mL). The combined filtrate was concentrated in vacuo and purified by flash chromatography (silica gel, 12 g, 10% to 100% EtOAc in PE), to afford compound 3d (110 mg, 71% yield). MS: calc'd 436, 438 [(M+H)$^+$], measured 436, 438 [(M+H)$^+$].

Step 2

Preparation of tert-butyl 4-[6-[[(2R,6S)-4-(8-cyano-5-quinolyl)-2,6-dimethyl-piperazin-1-yl]methyl]-3-pyridyl]piperazine-1-carboxylate (Compound 5c)

To a solution of 5-((3R,5S)-4-(5-bromopyridin-2-yl)methyl)-3,5-dimethylpiperazin-1-yl) quinoline-8-carbonitrile (compound 5b, 55 mg, 126 μmol) in dioxane (10 mL) was added tert-butyl piperazine-1-carboxylate (CAS: 57260-71-6, Accela ChemBio, Catalog: SY002528; 28.2 mg, 151 μmol), RuPhos Pd G3 (CAS: 1375325-68-0, Sigma-Aldrich, Catalog: 753246; 3.4 mg, 3.8 μmol) and sodium tert-butoxide (12.1 mg, 126 μmol). The reaction mixture was stirred at 80° C. for 14 hrs, then cooled to room temperature, diluted with water (20 mL), and extracted with EA (10 mL) twice. The combined organic layer was washed with brine, dried over $Na_2SO_4$, filtered and concentrated in vacuo. The residue was purified by flash chromatography (silica gel, 12 g, 20% to 100% EtOAc in PE) to afford compound 3c (50 mg, 73% yield). MS: calc'd 542 [(M+H)$^+$], measured 542 [(M+H)$^+$].

Step 3

Preparation of 5-[(3S,5R)-3,5-dimethyl-4-[(5-piperazin-1-yl-2-pyridyl) methyl]piperazin-1-yl]quinoline-8-carbonitrile (Example 5)

To a solution of tert-butyl 4-[6-[[(2R,6S)-4-(8-cyano-5-quinolyl)-2,6-dimethyl-piperazin-1-yl]methyl]-3-pyridyl]piperazine-1-carboxylate (compound 5c) (45 mg, 83 μmol) in DCM (2 mL) was added TFA (0.5 mL). The reaction mixture was stirred at room temperature for 3 hrs, then concentrated to afford a crude product, which was purified by prep-HPLC to afford Example 5 (39 mg, 98%). MS: calc'd 442 [(M+H)$^+$], measured 442 [(M+H)$^+$]. $^1$H NMR (400 MHz, METHANOL-d4) δ ppm 9.43 (dd, J=8.6, 1.4 Hz, 1H), 9.27 (dd, J=5.2, 1.4 Hz, 1H), 8.63 (d, J=2.8 Hz, 1H), 8.51 (d, J=8.2 Hz, 1H), 8.07-8.21 (m, 3H), 7.65 (d, J=8.3 Hz, 1H), 5.04 (s, 2H), 4.15-4.28 (m, 2H), 3.78-3.92 (m, 6H), 3.55-3.65 (m, 2H), 3.44-3.53 (m, 4H), 1.69 (d, J=6.5 Hz, 6H).

Example 6

5-[(3S,5R)-4-[[5-[4-[2-(Dimethylamino)acetyl]piperazin-1-yl]pyrimidin-2-yl]methyl]-3,5-dimethyl-piperazin-1-yl]quinoline-8-carbonitrile

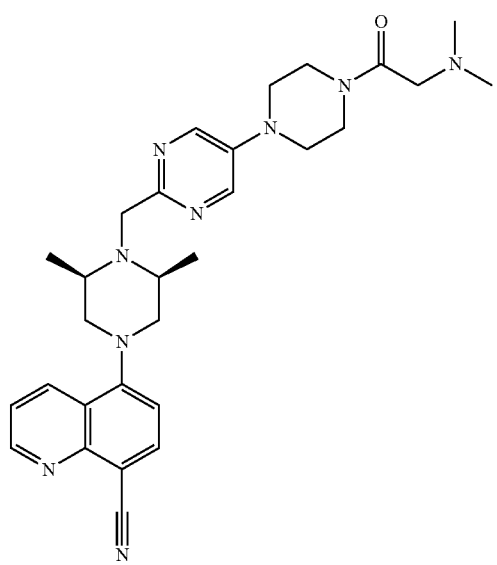

The title compound was prepared according to the following scheme:

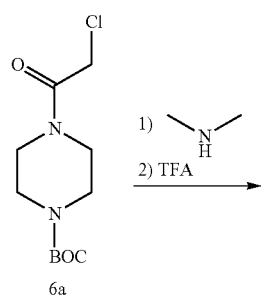

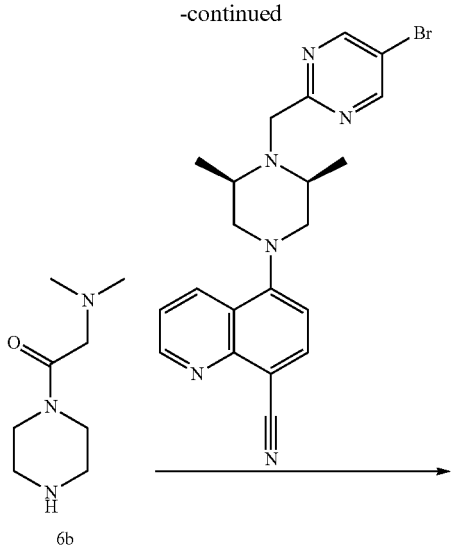

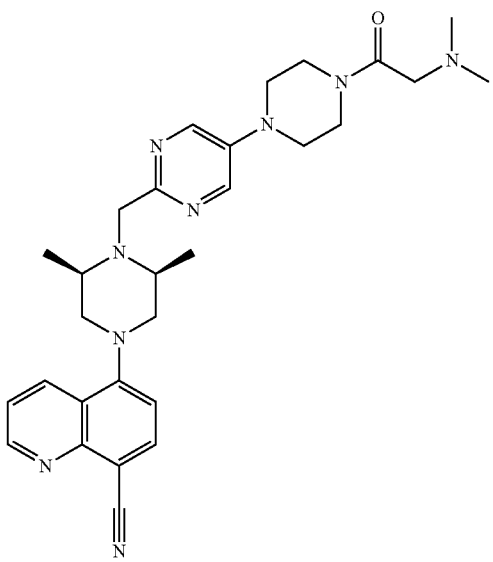 [SMILES: C[C@@H]1CN(c2ccc(C#N)c3ncccc23)C[C@H](C)N1Cc1ncc(N2CCN(C(=O)CN(C)C)CC2)cn1]

Step 1

Preparation of 2-(dimethylamino)-1-piperazin-1-yl-ethanone (compound 3b)

To a solution of tert-butyl 4-(2-chloroacetyl)piperazine-1-carboxylate (263 mg, 1 mmol) in acetonitrile (5 mL) was added dimethylamine hydrochloride (163 mg, 2 mmol) and K$_2$CO$_3$ (208 mg, 1.5 mmol). The reaction mixture was stirred at room temperature for 3 hrs. After filtered off the solid and washed with EA (10 mL), the combined filtrate was concentrated in vacuo. The residue was dissolved in DCM (1 mL), and TFA (1 mL) was added. The reaction mixture was stirred at room temperature for 3 hrs, then concentrated to afford a crude compound 6b (0.27 g, 94% yield). MS: calc'd 172 [(M+H)$^+$], measured 172 [(M+H)$^+$].

Step 2

Preparation of 5-[(3S,5R)-4-[[5-[4-[2-(dimethylamino)acetyl]piperazin-1-yl]pyrimidin-2-yl]methyl]-3,5-dimethyl-piperazin-1-yl]quinoline-8-carbonitrile (Example 6)

To a solution of 5-[(3R,5S)-4-[(5-bromopyrimidin-2-yl)methyl]-3,5-dimethyl-piperazin-1-yl]quinoline-8-carbonitrile (45 mg, 103 μmol,) in dioxane (10 mL) was added 2-(dimethylamino)-1-(piperazin-1-yl) ethan-1-one 2,2,2-trifluoroacetate (compound 6a, 35.2 mg, 123 μmol), RuPhos Pd G3 (CAS: 1445085-77-7, Sigma-Aldrich, Catalog: 763403; 2.75 mg, 3.1 μmol) and sodium tert-butoxide (29.7 mg, 309 μmol). The reaction mixture was stirred at 80° C. for 14 hrs, then cooled to room temperature, diluted with water (20 mL), and extracted with EA (10 mL) twice. The combined organic layer was washed with brine, dried over $Na_2SO_4$, filtered and concentrated in vacuo. The residue was purified by flash chromatography (silica gel, 12 g, 20% to 100% EtOAc in PE) to afford Example 6 (20 mg, 98% yield). MS: calc'd 528 [(M+H)$^+$], measured 528 [(M+H)$^+$]. $^1$H NMR (400 MHz, METHANOL-d$_4$) δ ppm 8.92 (dd, J=4.2, 1.6 Hz, 1H), 8.51 (s, 2H), 8.46 (dd, J=8.6, 1.5 Hz, 1H), 8.08 (d, J=8.1 Hz, 1H), 7.56 (dd, J=8.6, 4.3 Hz, 1H), 7.15 (d, J=8.2 Hz, 1H), 4.23 (s, 2H), 3.74-3.85 (m, 4H), 3.29-3.42 (m, 8H), 3.27 (s, 2H), 2.78 (t, J=11.2 Hz, 2H), 2.32 (s, 6H), 1.30 (d, J=6.1 Hz, 6H).

Example 7

5-[(3S,5R)-3,5-dimethyl-4-[[5-(4-methylpiperazin-1-yl)-2-pyridyl]methyl]piperazin-1-yl]quinoline-8-carbonitrile

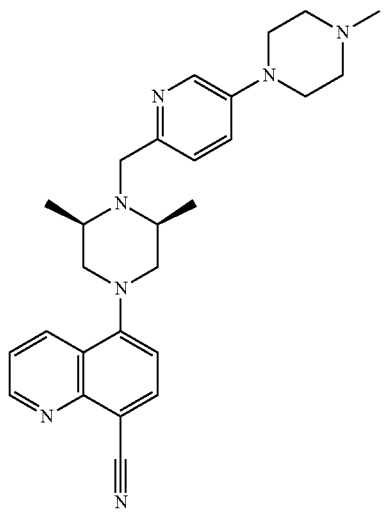 [SMILES: C[C@@H]1CN(c2ccc(C#N)c3ncccc23)C[C@H](C)N1Cc1ccc(N2CCN(C)CC2)cn1]

To a solution of 5-((3R,5S)-4-(5-bromopyridin-2-yl)methyl)-3,5-dimethylpiperazin-1-yl) quinoline-8-carbonitrile (compound 5b, 45 mg, 103 μmol) in dioxane (10 mL) was added 1-methylpiperazine (12.4 mg, 124 μmol), RuPhos Pd G3 (CAS: 1375325-68-0, Sigma-Aldrich, Catalog: 753246; 2.8 mg, 3.1 μmol) and sodium tert-butoxide (9.9 mg, 103 μmol). The reaction mixture was stirred at 80° C. for 14 hrs, then cooled to room temperature, diluted with water (20 mL), and extracted with EA (10 mL) twice. The combined organic layer was washed with brine, dried over $Na_2SO_4$, filtered and concentrated in vacuo. The residue was purified by flash chromatography (silica gel, 12 g, 20% to 100% EtOAc in PE) to afford Example 7 (47 mg, 98% yield). MS: calc'd 456 [(M+H)$^+$], measured 456 [(M+H)$^+$]. $^1$H NMR (400 MHz, METHANOL-d$_4$) δ ppm 8.96 (dd, J=4.2, 1.7 Hz, 1H), 8.58 (dd, J=8.6, 1.7 Hz, 1H), 8.20 (d, J=2.8 Hz, 1H), 8.13 (d, J=8.1 Hz, 1H), 7.62 (dd, J=8.6, 4.3 Hz, 1H), 7.57 (d, J=8.7 Hz, 1H), 7.43 (dd, J=8.8, 2.9 Hz, 1H), 7.21 (d, J=8.1 Hz, 1H), 4.00 (s, 2H), 3.39 (br d, J=11.9 Hz, 2H), 3.25-3.31 (m, 4H), 3.03-3.14 (m, 2H), 2.75-2.84 (m, 2H), 2.62-2.69 (m, 4H), 2.38 (s, 3H), 1.16 (d, J=6.1 Hz, 6H).

Example 8

5-[(3S,5R)-3,5-Dimethyl-4-[[5-(9-oxa-3,7-diazabicyclo[3.3.1]nonan-3-yl)-2-pyridyl]methyl]piperazin-1-yl]quinoline-8-carbonitrile

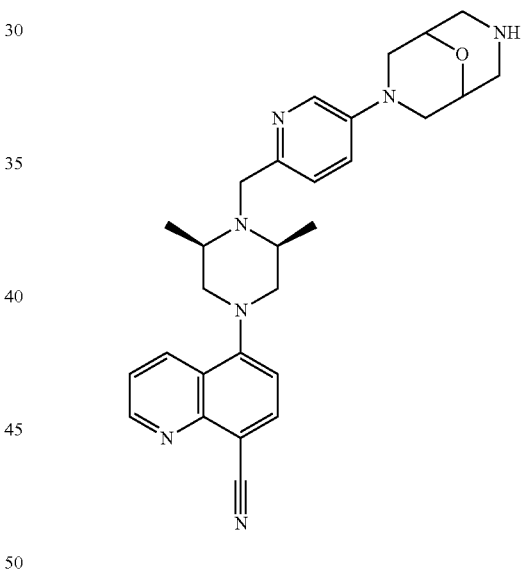

The title compound was prepared in analogy to the preparation of Example 5 by using tert-butyl 9-oxa-3,7-diazabicyclo[3.3.1]nonane-3-carboxylate instead of tert-butyl piperazine-1-carboxylate. Example 8 (10.0 mg) was obtained. MS: calc'd 484 [(M+H)$^+$], measured 484 [(M+H)$^+$]. $^1$H NMR (400 MHz, METHANOL-d$_4$) δ ppm 8.89 (dd, J=4.2, 1.5 Hz, 1H), 8.51 (dd, J=8.6, 1.3 Hz, 1H), 8.43 (d, J=2.7 Hz, 1H), 8.07 (d, J=7.9 Hz, 1H), 7.51-7.57 (m, 2H), 7.44-7.49 (m, 1H), 7.26 (d, J=8.1 Hz, 1H), 4.56-4.68 (m, 2H), 4.21 (br s, 2H), 3.93-4.06 (m, 2H), 3.83 (d, J=12.1 Hz, 2H), 3.38-3.65 (m, 7H), 3.19 (br s, 1H), 3.07-3.18 (m, 2H), 1.39 (br d, J=6.4 Hz, 6H)

Example 9

5-[(3R,5S)-3,5-Dimethyl-4-[[5-[[(3R,4S)-4-fluoropyrrolidin-3-yl]amino]-2-pyridyl]methyl]piperazin-1-yl]quinoline-8-carbonitrile

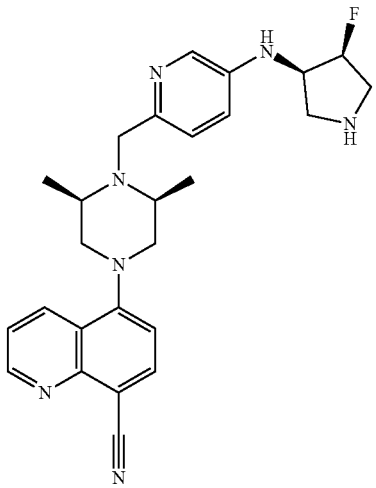 [SMILES: C[C@@H]1CN(c2ccc(C#N)c3ncccc23)C[C@H](C)N1Cc1ccc(N[C@@H]2CNC[C@@H]2F)cn1]

The title compound was prepared in analogy to the preparation of Example 5 by using tert-butyl (3R,4S)-3-amino-4-fluoropyrrolidine-1-carboxylate (25.2 mg, 123 µmol, Eq: 1.2) instead of tert-butyl piperazine-1-carboxylate. Example 9 (14.0 mg) was obtained. MS: calc'd 460 [(M+H)+], measured 460 [(M+H)+]. $^1$H NMR (400 MHz, METHANOL-$d_4$) δ ppm 8.93 (dd, J=4.3, 1.6 Hz, 1H), 8.53 (dd, J=8.6, 1.7 Hz, 1H), 8.09 (d, J=8.1 Hz, 1H), 8.03 (d, J=2.7 Hz, 1H), 7.59 (dd, J=8.6, 4.3 Hz, 1H), 7.44 (d, J=8.6 Hz, 1H), 7.12-7.22 (m, 2H), 5.07-5.26 (m, 1H), 3.91-4.09 (m, 3H), 3.36-3.42 (m, 2H), 3.35-3.34 (m, 1H), 3.12-3.29 (m, 2H), 2.98-3.11 (m, 2H), 2.77 (q, J=10.1 Hz, 3H), 1.17 (d, J=6.1 Hz, 6H).

Example 10

5-[(3R,5S)-3,5-Dimethyl-4-[[5-[4-(pyrrolidine-2-carbonyl)piperazin-1-yl]-2-pyridyl]methyl]piperazin-1-yl]quinoline-8-carbonitrile

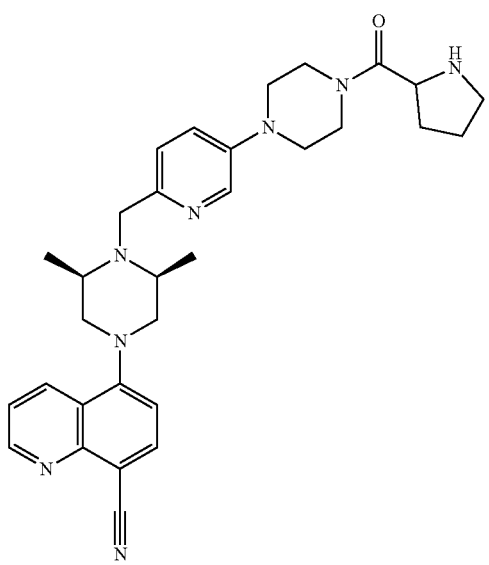 [SMILES: C[C@@H]1CN(c2ccc(C#N)c3ncccc23)C[C@H](C)N1Cc1ccc(N2CCN(C(=O)C3CCCN3)CC2)cn1]

To a stirred solution of 5-((3R,5S)-3,5-dimethyl-4-((5-(piperazin-1-yl)pyridin-2-yl) methyl)piperazin-1-yl)quinoline-8-carbonitrile (Example 5, 20 mg, 45 mmol) and tert-butoxycarbonyl)proline (9.75 mg, 45.3 µmol) in DMF (2 mL) at room temperature was added HATU (17.2 mg, 45.3 µmol) and DIEPA (5.8 mg, 45 µmol). The reaction mixture was stirred for 3 hrs at room temperature before concentrated in vacuo.

The residue was dissolved in DCM (2 mL) and TFA (1 mL) was added. The reaction mixture was stirred at room temperature for 30 min, then concentrated to afford a crude product, which was purified by prep-HPLC to afford Example 10 (11 mg, 51% yield). MS: calc'd 539 [(M+H)+], measured 539 [(M+H)+]. $^1$H NMR (400 MHz, METHANOL-$d_4$) δ ppm 8.96 (dd, J=4.2, 1.7 Hz, 1H), 8.58 (dd, J=8.6, 1.7 Hz, 1H), 8.23 (d, J=2.8 Hz, 1H), 8.13 (d, J=7.9 Hz, 1H), 7.56-7.65 (m, 2H), 7.46 (dd, J=8.7, 2.9 Hz, 1H), 7.21 (d, J=8.2 Hz, 1H), 3.97-4.08 (m, 3H), 3.68-3.86 (m, 4H), 3.39 (br d, J=11.7 Hz, 2H), 3.23-3.32 (m, 4H), 3.15-3.22 (m, 1H), 3.04-3.14 (m, 2H), 2.76-2.89 (m, 3H), 2.20-2.31 (m, 1H), 1.67-1.94 (m, 3H), 1.16 (d, J=6.2 Hz, 6H).

Example 11

5-[(3S,5R)-4-[[5-[4-[2-(Dimethylamino)acetyl]piperazin-1-yl]-2-pyridyl]methyl]-3,5-dimethyl-piperazin-1-yl]quinoline-8-carbonitrile

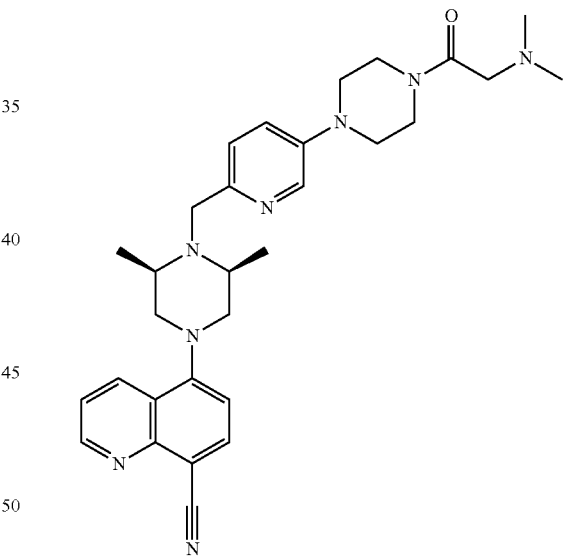

The title compound was prepared in analogy to the preparation of Example 6 by using 5-((3R,5S)-4-((5-bromopyridin-2-yl)methyl) -3,5-dimethylp iperazin-1-yl)quino line-8-carbo nitrile instead of 5-[(3R,5S)-4-[(5-bromopyrimidin-2-yl)methyl]-3,5-dimethyl-piperazin-1-yl]quinoline-8-carbonitrile. Example 11 (66 mg) was obtained. MS: calc'd 527 [(M+H)+], measured 527 [(M+H)+]. $^1$H NMR (400 MHz, METHANOL-$d_4$) δ ppm 8.97 (dd, J=4.3, 1.6 Hz, 1H), 8.60 (dd, J=8.7, 1.6 Hz, 1H), 8.47 (t, J=1.6 Hz, 1H), 8.15 (d, J=7.9 Hz, 1H), 7.65 (dd, J=8.6, 4.3 Hz, 1H), 7.55 (d, J=1.7 Hz, 2H), 7.35 (d, J=8.1 Hz, 1H), 4.70 (s, 2H), 4.36 (s, 2H), 4.01-4.15 (m, 2H), 3.80-3.89 (m, 2H), 3.57-3.69 (m, 4H), 3.43 (dt, J=14.4, 5.3 Hz, 4H), 3.27 (dd, J=13.3, 11.4 Hz, 2H), 3.00 (s, 6H), 1.52 (d, J=6.5 Hz, 6H).

Example 12

5-[(3R,5S)-4-[[4-[2-(Hydroxymethyl)piperazin-1-yl]phenyl]methyl]-3,5-dimethyl-piperazin-1-yl]quinoline-8-carbonitrile

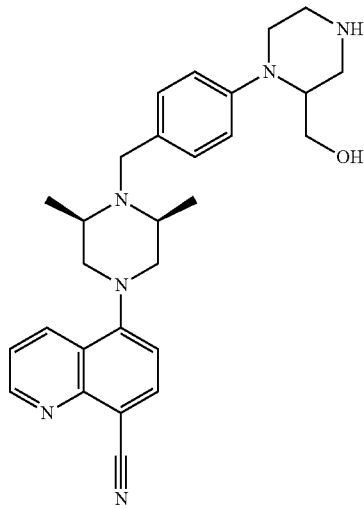 [SMILES: C[C@@H]1CN(c2ccc(C#N)c3ncccc23)C[C@H](C)N1Cc1ccc(N2CCNCC2CO)cc1]

The title compound was prepared in analogy to the preparation of Example 1 by using tert-butyl 3-(hydroxymethyl)piperazine-1-carboxylate (CAS: 301673-16-5, Accela ChemBio, Catalog: SY008701) instead of tert-butyl piperazine-1-carboxylate. Example 12 (10.0 mg) was obtained. MS: calc'd 471 [(M+H)⁺], measured 471 [(M+H)⁺]. ¹H NMR (400 MHz, METHANOL-d₄) δ ppm 8.89-9.10 (m, 1H), 8.51 (br d, J=8.6 Hz, 1H), 8.18 (d, J=7.9 Hz, 1H), 7.50-7.73 (m, 3H), 7.33 (br d, J=7.9 Hz, 1H), 7.17 (d, J=8.7 Hz, 2H), 4.70 (s, 2H), 4.26 (br s, 1H), 3.88-3.97 (m, 1H), 3.59-3.86 (m, 8H), 3.54 (br d, J=12.7 Hz, 1H), 3.45 (dd, J=12.8, 4.5 Hz, 1H), 3.24-3.31 (m, 1H), 3.17 (br t, J=11.6 Hz, 2H), 1.69 (br d, J=6.2 Hz, 6H).

Example 13

5-[(3R,5S)-3,5-Dimethyl-4-[2-oxo-2-(2-piperazin-1-yl-7,8-dihydro-5H-1,6-naphthyridin-6-yl)ethyl]piperazin-1-yl]quinoline-8-carbonitrile

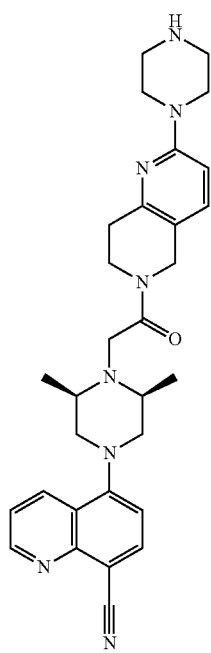 [SMILES: C[C@@H]1CN(c2ccc(C#N)c3ncccc23)C[C@H](C)N1CC(=O)N1CCc2nc(N3CCNCC3)ccc2C1]

The title compound was prepared according to the following scheme:

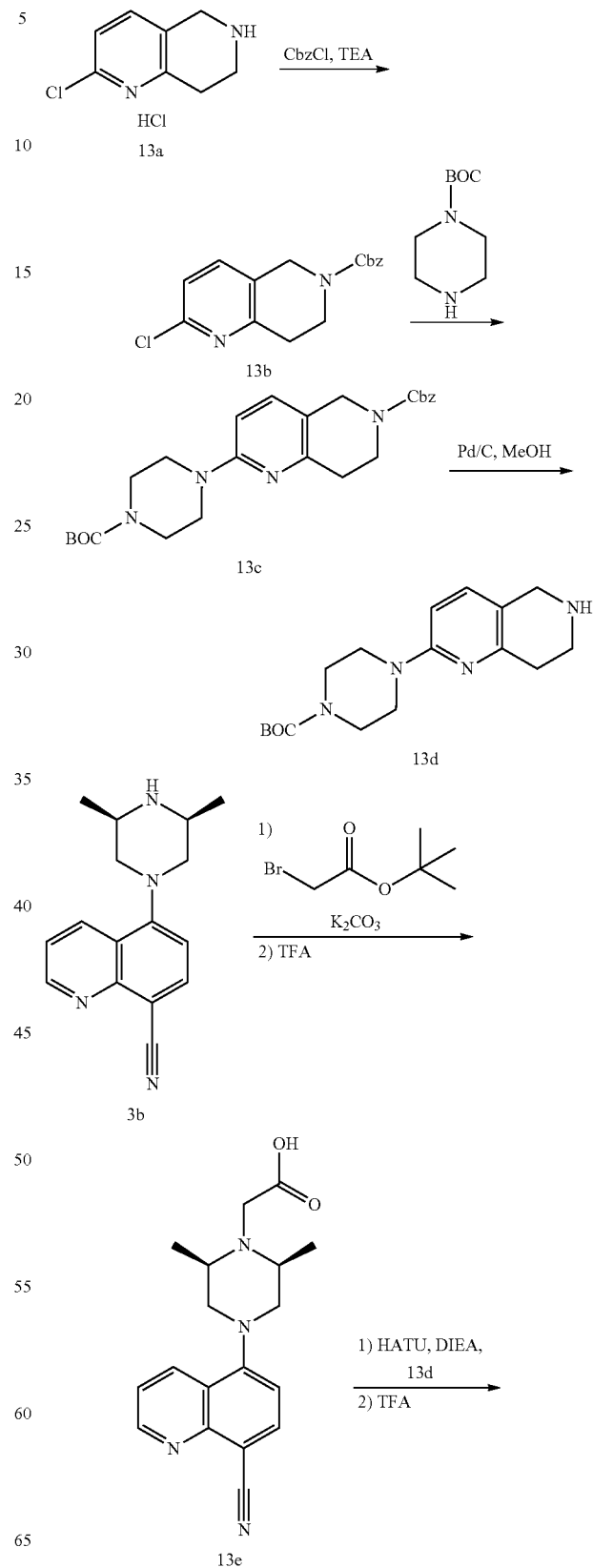

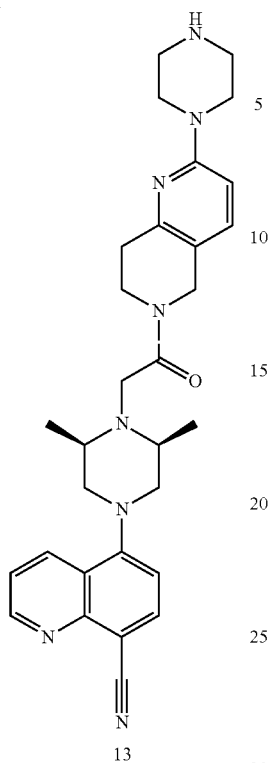

13

Step 1

Preparation of Benzyl 2-chloro-7,8-dihydro-5H-1,6-naphthyridine-6-carboxylate (Compound 13b)

To solution of 2-chloro-5,6,7,8-tetrahydro-1,6-naphthyridine hydrochloride (compound 13a, CAS: 766545-20-4, PharmaBlock, Catalog: PB06676-01, 1.0 g, 4.9 mmol) in DCM (25 mL) was added triethylamine (5.9 mL, 42.6 mmol), benzyl chloroformate (831.8 mg, 4.9 mmol). The resultant mixture was stirred at room temperature for 2 hrs, and then diluted with $H_2O$ (50 mL) and extracted with DCM (30 mL) twice. The combined organic layer was washed with brine, dried over $Na_2SO_4$, filtered and concentrated in vacuo. The residue was purified by flash chromatography (silica gel, 120 g, 9% to 17% EtOAc in PE) to afford compound 13b (450 mg, 26% yield). MS: calc'd 303 [(M+H)$^+$], measured 303 [(M+H)$^+$].

Step 2

Preparation of Benzyl 2-(4-tert-butoxycarbonylpiperazin-1-yl)-7,8-dihydro-5H-1,6-naphthyridine-6-carboxylate (Compound 13c)

To a solution of 1-Boc-piperazine (CAS 57260-71-6, PharmaBlock, Catalog: PB002528, 415.2 mg, 2.2 mmol) and benzyl 2-chloro-7,8-dihydro-5H-1,6-naphthyridine-6-carboxylate (compound 13b, 450.0 mg, 1.5 mmol) in dioxane (25 mL) was added palladium (II) acetate (33.37 mg, 0.150 mmol), sodium tert-butoxide (214.26 mg, 2.23 mmol) and (R)-binap (CAS 98327-87-8, PharmaBlock, Catalog: PB92651, 185.1 mg, 0.3 mmol). The resultant mixture was stirred at 100° C. for 5 hrs under $N_2$, before diluted with water (50 mL) and extracted with EA (30 mL) twice. The combined organic layer was dried over $Na_2SO_4$, filtered and concentrated in vacuo. The residue was purified by flash chromatography (silica gel, 80 g, 17% to 25% EtOAc in PE) to afford compound 1d (330 mg, 43% yield). MS: calc'd 453 [(M+H)$^+$], measured 453 [(M+H)$^+$].

Step 3

Preparation of tert-butyl 4-(5,6,7,8-tetrahydro-1,6-naphthyridin-2-yl) piperazine-1-carboxylate (Compound 13d)

To a solution of benzyl 2-(4-tert-butoxycarbonylpiperazin-1-yl)-7,8-dihydro-5H-1,6-naphthyridine-6-carboxylate (compound 13c, 330 mg, 0.73 mmol) in methanol (20 mL) was added Pd/C (80 mg, 0.73 mmol). The resultant mixture was degassed, followed by charging with hydrogen gas for three rounds. After stirred for 0.5 h at room temperature, the reaction mixture was filtered through Celite. The filtrate was concentrated in vacuo. The residue was purified by flash chromatography (silica gel, 12 g, 10% to 90% EtOAc in PE) to afford compound 13d (200 mg, 84% yield). MS: calc'd 319 [(M+H)$^+$], measured 319 [(M+H)$^+$].

Step 4

Preparation of 2-[(2R,6S)-4-(8-cyano-5-quinolyl)-2,6-dimethyl-piperazin-1-yl]acetic acid (Compound 13e)

To a solution of 5-[(3R,5S)-3,5-dimethylpiperazin-1-yl] quinoline-8-carbonitrile (compound 3b, 1000 mg, 3.8 mmol) in ACN (40 mL) was added sodium iodide (56.3 mg, 0.38 mmol) and tert-butyl bromoacetate (1098 mg, 5.6 mmol). The resultant mixture was stirred at 65° C. for 4 hrs, then cooled to room temperature, diluted with $H_2O$ (50 mL) and extracted with EtOAc (50 mL) twice. The combined organic layer was washed with brine, dried over $Na_2SO_4$, filtered and concentrated in vacuo.

The residue was dissolved in DCM (30 mL) and TFA (5 mL) was added. The reaction mixture was stirred at room temperature for 12 hrs, then concentrated to afford a crude product compound 13e (1.0 g, 68% yield). MS: calc'd 325 [(M+H)$^+$], measured 325 [(M+H)$^+$].

Step 5

Preparation of 5-[(3R,5S)-3,5-Dimethyl-4-[2-oxo-2-(2-piperazin-1-yl-7,8-dihydro-5H-1,6-naphthyridin-6-yl) ethyl]piperazin-1-yl]quinoline-8-carbonitrile (Compound 13)

To a stirred solution of 2-[(2R,6S)-4-(8-cyano-5-quinolyl)-2,6-dimethyl-piperazin-1-yl]acetic acid (compound 13e, 50.0 mg, 0.150 mmol) and HATU (70.3 mg, 0.18 mmol) and DIEPA (0.08 mL, 0.460 mmol) in DMF (2 mL) was added tert-butyl 4-(5,6,7,8-tetrahydro-1,6-naphthyridin-2-yl) piperazine-1-carboxylate (compound 13d, 54.53 mg, 0.170 mmol) at room temperature. The reaction mixture was stirred for 3 hrs at room temperature and then concentrated in vacuo.

The residue was dissolved in DCM (2 mL) and TFA (1 mL) was added. The reaction mixture was stirred at room temperature for 30 min, then concentrated to afford a crude product, which was purified by prep-HPLC to afford Example 13 (18 mg, 22% yield). MS calc'd 525 [(M+H)$^+$]; measured 525 [(M+H)$^+$]. $^1$H NMR (400 MHz, METHA- NOL-d$_4$) δ=9.05 (d, J=4.2 Hz, 1H), 8.69 (br d, J=8.4 Hz, 1H), 8.23 (d, J=8.1 Hz, 1H), 7.72 (dd, J=4.2, 8.6 Hz, 1H), 7.51 (br d, J=8.8 Hz, 1H), 7.44 -7.32 (m, 1H), 6.92 -6.82 (m, 1H), 4.92 (br s, 4H), 4.75 (s, 2H), 4.50 -4.35 (m, 1H), 4.30 -4.07 (m, 2H), 4.00 (t, J=6.1 Hz, 1H), 3.95 -3.86 (m, 1H), 3.86 -3.80 (m, 4H), 3.64 (br s, 2H), 3.40 -3.34 (m, 3H), 3.04 (br t, J=5.7 Hz, 1H), 2.92 (t, J=6.0 Hz, 1H), 1.41 (br s, 6H).

Example 14

5-[(3R,5S)-3,5-Dimethyl-4-[2-oxo-2-(6-piperazin-1-yl-3,4-dihyrdo-1H-isoquinolin-2-yl) ethyl]piperazin-1-yl]quinoline-8-carbonitrile

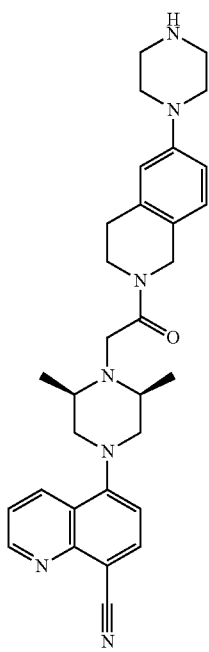 [SMILES: C[C@@H]1CN(c2ccc(C#N)c3ncccc23)C[C@H](C)N1CC(=O)N1CCc2cc(N3CCNCC3)ccc2C1]

The title compound was prepared in analogy to the preparation of Example 13 by using 6-bromo-1,2,3,4-tetrahydroisoquinoline hydrochloride (CAS: 215798-19-9, PharmaBlock, Catalog: PB07543-1) instead of 2-chloro-5,6,7,8-tetrahydro-1,6-naphthyridine hydrochloride. Example 14 (5.2 mg) was obtained. MS: calc'd 524 [(M+H)$^+$], measured 524 [(M+H)$^+$]. $^1$H NMR (400 MHz, METHANOL-d$_4$) δ ppm 8.92 (dd, J=1.6, 4.3 Hz, 1H), 8.63 -8.51 (m, 1H), 8.18 -8.05 (m, 1H), 7.65 -7.56 (m, 1H), 7.37 -7.22 (m, 1H), 7.06 (dd, J=8.4, 13.1 Hz, 1H), 6.84 (br t, J=7.8 Hz, 1H), 6.79 (br d, J=4.3 Hz, 1H), 4.63 (s, 2H), 4.54 (br s, 1H), 4.17 -3.89 (m, 2H), 3.80 -3.73 (m, 1H), 3.68 (br s, 1H), 3.61 -3.39 (m, 2H), 3.35 -3.24 (m, 10H), 3.17 -3.01 (m, 1H), 2.91 (br t, J=5.8 Hz, 1H), 2.81 (br t, J=6.1 Hz, 1H), 1.37 -1.17 (m, 6H).

Example 15

5-[(3R,5S)-3,5-dimethyl-4-[2-pxp-2-(7-piperazin-1-yl-3,4-dihydro-1H-isoquinolin-2-yl) ethyl]piperazin-1-yl]quinoline-8-carbonitrile

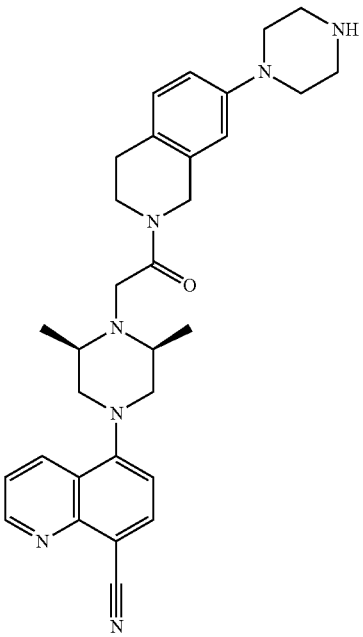 [SMILES: C[C@@H]1CN(c2ccc(C#N)c3ncccc23)C[C@H](C)N1CC(=O)N1CCc2ccc(N3CCNCC3)cc2C1]

The title compound was prepared in analogy to the preparation of Example 13 by using 7-bromo-1,2,3,4-tetrahydroisoquinoline hydrochloride (CAS: 2200274-73-4, Oakwood Chemical, Catalog: 077414) instead of 2-chloro-5,6,7,8-tetrahydro-1,6-naphthyridine hydrochloride. Example 15 (44 mg) was obtained. MS: calc'd 524 [(M+H)$^+$], measured 524 [(M+H)$^+$]. $^1$H NMR (400 MHz, METHANOL-d$_4$) δ ppm 9.05 (dd, J=1.5, 4.2 Hz, 1H), 8.69 (br s, 1H), 8.24 (d, J=7.9 Hz, 1H), 7.72 (dd, J=4.2, 8.6 Hz, 1H), 7.41 (br s, 1H), 7.18 (br d, J=8.4 Hz, 1H), 6.99 -6.93 (m, 1H), 6.90 (s, 1H), 4.80 (s, 2H), 4.67 (br s, 1H), 4.37 (br s, 1H), 4.29 -4.00 (m, 2H), 3.91 (t, J=6.0 Hz, 1H), 3.79 (br s, 1H), 3.66 (br s, 1H), 3.56 (br s, 1H), 3.44 -3.35 (m, 10H), 3.04 -2.83 (m, 2H), 1.42 (br s, 6H).

Example 16

5-[(3R,5S)-3,5-Dimethyl-4-[2-oxo-2-(5-piperazin-1-ylisoindolin-2-yl)ethyl]piperazin-1-yl]quinoline-8-carbonitrile

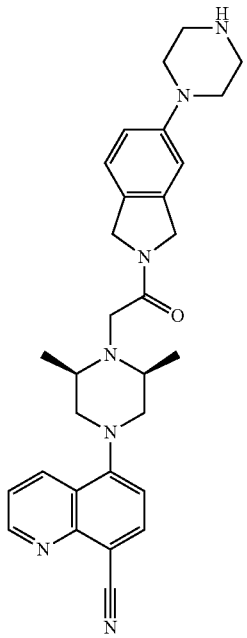 [SMILES: C[C@@H]1CN(c2ccc(C#N)c3ncccc23)C[C@H](C)N1CC(=O)N1Cc2ccc(N3CCNCC3)cc2C1]

The title compound was prepared in analogy to the preparation of Example 13 by using 5-bromoisoindoline hydrochloride (CAS: 919346-89-7, PharmaBlock, Catalog: PBY2010168-01) instead of 2-chloro-5,6,7,8-tetrahydro-1,6-naphthyridine hydrochloride. Example 15 (22 mg) was obtained. MS: calc'd 510 [(M+H)$^+$], measured 510 [(M+H)$^+$]. 1 H NMR (400 MHz, METHANOL-d$_4$) δ ppm 9.43 (br dd, J=19.2, 8.3 Hz, 1H), 9.24-9.32 (m, 1H), 8.48-8.58 (m, 1H), 8.19 (dd, J=8.6, 5.3 Hz, 1H), 7.62-7.79 (m, 1H), 7.35-7.58 (m, 3H), 5.11-5.25 (m, 2H), 4.91 (br d, J=14.7 Hz, 2H), 4.71 (br d, J=3.3 Hz, 1H), 4.45 (br d, J=3.1 Hz, 1H), 4.25-4.40 (m, 2H), 3.43-3.89 (m, 12H), 1.41-1.55 (m, 6H).

Example 17

2-[4-(8-Cyano-5-quinolyl)-2-methyl-piperazin-1-yl]-N-(4-piperazin-1-ylpheny)acetamide

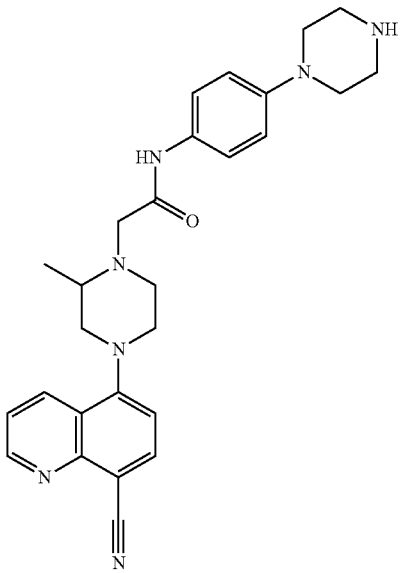 [SMILES: CC1CN(c2ccc(C#N)c3ncccc23)CCN1CC(=O)Nc1ccc(N2CCNCC2)cc1]

The title compound was prepared according to the following scheme:

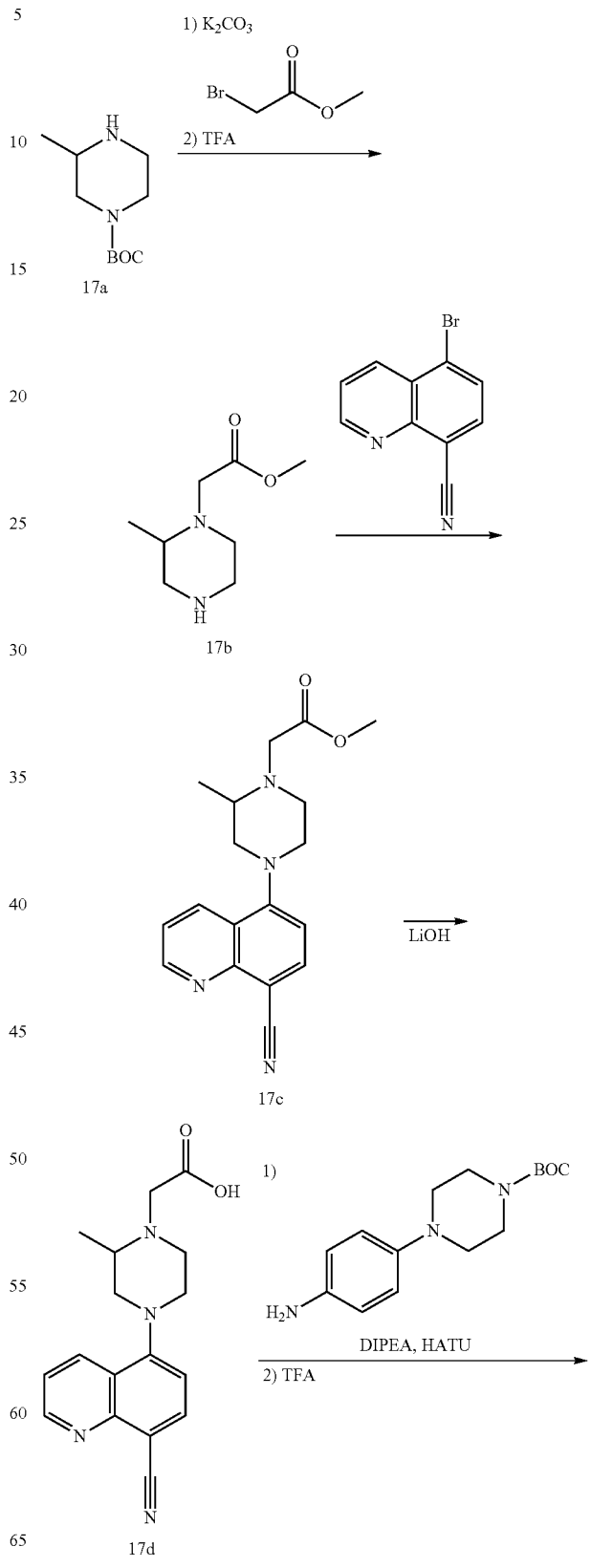

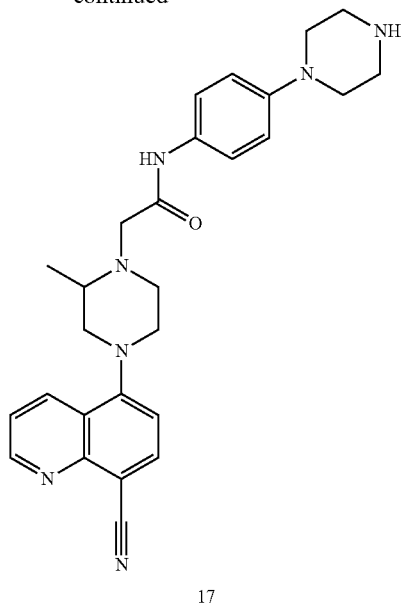

17

Step 1

Preparation of methyl 2-(2-methylpiperazin-1-yl)acetate (Compound 17b)

To solution of tert-butyl 3-methylpiperazine-1-carboxylate (CAS: 120737-59-9, Accela Chembio, Catalog: SY002666, 1.0 g, 5.0 mmol) in acetonitrile (15 mL) was added $K_2CO_3$ (690 mg, 5.0 mmol) and methyl 2-bromoacetate (764 mg, 5.0 mmol). The resultant mixture was stirred at 80° C. for 3 hrs, before cooled to room temperature and filtered through Celite. The filter cake as washed with EA (10 mL) twice. The combined organic layer was concentrated in vacuo, and the residue was purified by flash chromatography (silica gel, 25 g, 9% to 100% EtOAc in PE).

The purified intermediate was dissolved in DCM (2 mL) and TFA (1 mL) was added. The reaction mixture was stirred at room temperature for 30 min, then concentrated to afford a crude compound 17b (500 mg, 58% yield). MS calc'd 173 [(M+H)$^+$]; measured 173 [(M+H)$^+$].

Step 2

Preparation of Benzyl 2-chloro-7,8-dihydro-5H-1,6-naphthyridine-6-carboxylate (Compound 17c)

To a solution of 5-bromoquinoline-8-carbonitrile (CAS: 96-32-2, Alfa Aesar, Catalog: A10605, 300 mg, 1.29 mmol) in dioxane (10 mL) was added methyl 2-(2-methylpiperazin-1-yl)acetate (compound 17b, 200 mg, 1.2 mmol), RuPhos G2 (CAS: 1375325-68-0, Sigma-Aldrich, Catalog: 753246, 27.1 mg, 34.8 μmol) and $Cs_2CO_3$ (568 mg, 1.7 mmol). The reaction mixture was stirred at 80° C. for 13 hrs, then cooled to room temperature. The reaction mixture was filtered and the filtrate was diluted with water (10 mL), then extracted with EA (40 mL) for three times. The combined organic layer was washed with brine, dried over $Na_2SO_4$, filtered and concentrated in vacuo. The residue was purified by flash chromatography (silica gel, 40 g, 16% to 100% EtOAc in PE) to afford compound 17c (300 mg, 80% yield). MS calc'd 325 [(M+H)$^+$]; measured 325 [(M+H)$^+$].

Step 3

Preparation of 2-[4-(8-cyano-5-quinolyl)-2-methyl-piperazin-1-yl]acetic acid (Compound 17d)

To a solution of methyl 2-(4-(8-cyanoquinolin-5-yl)-2-methylpiperazin-1-yl)acetate (compound 17c, 300 mg, 925 μmol) in THF (5 mL) and water (5 mL) wad added lithium hydroxide monohydrate (58.3 mg, 1.4 mmol). The resultant mixture was stirred at room temperature for 4 hrs, then neutralized by 1 M HCl. The mixture was concentrated in vacuo to afford a light yellow solid which was directly used for next step without further purification.

Step 4

Preparation of 2-[4-(8-cyano-5-quinolyl)-2-methyl-piperazin-1-yl]-N-(4-piperazin-1-ylphenyl) acetamide (Example 17)

To a stirred solution of 2-(4-(8-cyanoquinolin-5-yl)-2-methylpiperazin-1-yl)acetic acid (compound 17d, 35.0 mg, 113 μmol) and HATU (51.5 mg, 135 μmol) and DIEPA (29.2 mg, 226 μmol) in DMF (2 mL) was added tert-butyl 4-(4-aminophenyl)piperazine-1-carboxylate (37.5 mg, 135 μmol) at room temperature. The reaction mixture was stirred for 3 hrs at room temperature before being concentrated in vacuo.

The residue was dissolved in DCM (2 mL) and TFA (1 mL) was added. The reaction mixture was stirred at room temperature for 30 min, then concentrated in vacuo to afford a crude product, which was purified by prep-HPLC to afford Example 17 (39 mg, 57% yield). MS calc'd 470 [(M+H)$^+$]; measured 470 [(M+H)$^+$]. $^1$H NMR (400MHz, METHA-NOL-$d_4$) δ=9.02 (dd, J=4.6, 1.5 Hz, 1H), 8.89 (d, J=8.6 Hz, 1H), 8.24 (d, J=8.1 Hz, 1H), 7.79 (dd, J=8.6, 4.6 Hz, 1H), 7.53 (d, J=9.0 Hz, 2H), 7.40 (br d, J=7.9 Hz, 1H), 7.04 (d, J=9.0 Hz, 2H), 4.51 (br d, J=16.1 Hz, 1H), 3.96-4.29 (m, 3H), 3.92 (br d, J=12.1 Hz, 1H), 3.74 (br t, J=10.1 Hz, 1H), 3.56-3.69 (m, 2H), 3.31-3.47 (m, 9H), 1.42-1.59 (m, 3H)

Example 18

2-[4-(8-Cyano-5-quinolyl)-2-methyl-piperazin-1yl]-N-(1,2,3,4-tetrahydroisoquinolin-6-yl)acetamide

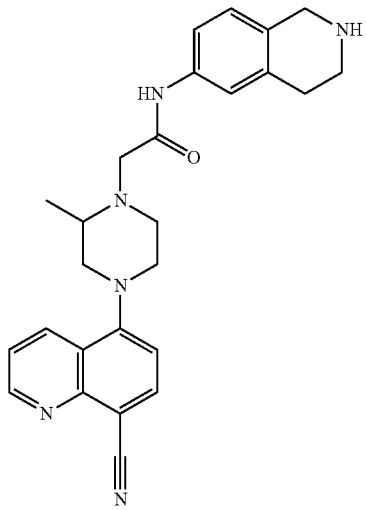 [SMILES: CC1CN(c2ccc(C#N)c3ncccc23)CCN1CC(=O)Nc1ccc2c(c1)CCNC2]

The title compound was prepared in analogy to the preparation of Example 17 by using tert-butyl 6-amino-3,4-dihydro-1H-isoquinoline-2-carboxylate (CAS: 164148-92-9, PharmaBlock, Catalog: PB03559) instead of tert-butyl 4-(4-aminophenyl)piperazine-1-carboxylate. Example 18 (40 mg) was obtained. MS: calc'd 441 [(M+H)+], measured 441 [(M+H)+]. $^1$H NMR (400 MHz, METHANOL-$d_4$) δ ppm 9.09 (dd, J=4.5, 1.4 Hz, 1H), 8.88 (br d, J=8.4 Hz, 1H), 8.29 (d, J=7.9 Hz, 1H), 7.83 (dd, J=8.6, 4.5 Hz, 1H), 7.65 (s, 1H), 7.57 (dd, J=8.3, 2.0 Hz, 1H), 7.47 (br d, J=7.9 Hz, 1H), 7.28 (d, J=8.4 Hz, 1H), 4.66 (br d, J=15.6 Hz, 1H), 4.40-4.27 (m, 3H), 4.25 (br d, J=15.8 Hz, 1H), 4.04 (br d, J=11.6 Hz, 1H), 3.86 (br t, J=10.1 Hz, 1H), 3.62-3.80 (m, 2H), 3.46-3.59 (m, 3H), 3.34-3.40 (m, 1H), 3.13 (t, J=6.4 Hz, 2H), 1.54-1.72 (m, 3H).

Example 19

5-[3-methyl-4-[2-[4-(1-methyl-4-piperidyl)-1-piperidyl]-2-oxo-ethyl]piperazin-1-yl]quinoline-8-carbonitrile

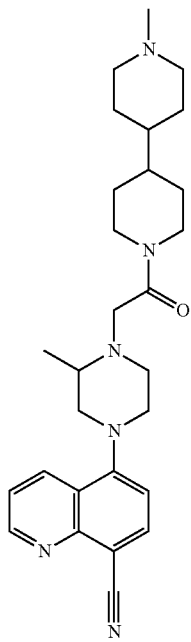 [SMILES: CC1CN(c2ccc(C#N)c3ncccc23)CCN1CC(=O)N1CCC(C2CCN(C)CC2)CC1]

To a stirred solution of 2-(4-(8-cyanoquinolin-5-yl)-2-methylpiperazin-1-yl)acetic acid (compound 17d, 35.0 mg, 113 μmol) and HATU (51.5 mg, 135 μmol) and DIEPA (29.2 mg, 226 μmol) in DMF (2 mL) was added 1-methyl-4,4'-bipiperidine (CAS: 122373-80-2, J&K Scientific, Catalog: K66-4018200, 24.7 mg, 135 μmol) at room temperature. The reaction mixture was stirred for 3 hrs at room temperature before concentrated in vacuo. The residue was dissolved in EA (20 mL) and washed with aqueous NaOH (0.5 N, 5 mL) and water (5 mL). The organic layer was dried over anhydrous $Na_2SO_4$, filtered and concentrated in vacuo to afford a crude product, which was purified by prep-HPLC to afford Example 19 (25 mg, 45% yield). MS calc'd 475 [(M+H)+]; measured 475 [(M+H)+]. $^1$H NMR (400 MHz, METHANOL-$d_4$) δ=8.96 (dd, J=4.2, 1.6 Hz, 1H), 8.60 (dd, J=8.6, 1.6 Hz, 1H), 8.11 (d, J=8.1 Hz, 1H), 7.62 (dd, J=8.6, 4.3 Hz, 1H), 7.21 (dd, J=8.1, 2.1 Hz, 1H), 4.48-4.64 (m, 1H), 4.19-4.38 (m, 1H), 3.68-3.94 (m, 1H), 3.35-3.42 (m, 1H), 2.71-3.19 (m, 9H), 2.53-2.68 (m, 1H), 2.26 (d, J=3.1 Hz, 3H), 1.68-2.03 (m, 7H), 1.24-1.47 (m, 4H), 1.22 (d, J=6.0 Hz, 3H), 1.12 (td, J=12.0, 3.8 Hz, 2H).

Example 20

The following tests were carried out in order to determine the activity of the compounds of formula (I) in HEK293-Blue-hTLR-7/8/9 cells assay.

HEK293-Blue-hTLR-7 Cells Assay

A stable HEK293-Blue-hTLR-7 cell line was purchased from InvivoGen (Cat.#: hkb-htlr7, San Diego, California, USA). These cells were originally designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore the reporter expression was declined by TLR7 antagonist under the stimulation of a ligand, such as R848 (Resiquimod), for incubation of 20 hrs. The cell culture supernatant SEAP reporter activity was determined using QUANTI-Blue™ kit (Cat.#: rep-qb1, Invivogen, San Diego, Ca, USA) at a wavelength of 640 nm, a detection medium that turns purple or blue in the presence of alkaline phosphatase.

HEK293-Blue-hTLR7 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 20 uM R848 in above DMEM, perform incubation under 37° C. in a $CO_2$ incubator for 20 hrs. Then 20 μL of the supernatant from each well was incubated with 180 pL Quanti-blue substrate solution at 37° C. for 2 hrs and the absorbance was read at 620-655 nm using a spectrophotometer. The signalling pathway that TLR7 activation leads to downstream NF-κB activation has been widely accepted, and therefore similar reporter assay was modified for evaluating TLR7 antagonist.

HEK293-Blue-hTLR-8 Cells Assay

A stable HEK293-Blue-hTLR-8 cell line was purchased from InvivoGen (Cat.#: hkb-htlr8, San Diego, California, USA). These cells were originally designed for studying the stimulation of human TLR8 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and. AP-1 via stimulating HEK-Blue hTLR8 cells with TLR8 ligands. Therefore the reporter expression was declined by TLR8 antagonist under the stimulation of a ligand, such as R848, for incubation of 20 hrs. The cell culture supernatant SEAP reporter activity was determined using QUANTI-Blue™ kit (Cat.#: rep-qb1, Invivogen, San Diego, Ca, USA) at a wavelength of 640 nm, a detection medium that tunas purple or blue in the presence of alkaline phosphatase.

HEK293-Blue-hTLR8 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 60 uM R848 in above DMEM, perform incubation under 37° C. in a $CO_2$ incubator for 20 hrs. Then 20 μL of the supernatant from each well was incubated with 180 pL Quanti-blue substrate solution at 37° C. for 2 hrs and the absorbance was read at 620-655 nm using a spectrophotometer. The signalling pathway that TLR8 activation leads to downstream NF-κB activation has been widely accepted, and therefore similar reporter assay was modified for evaluating TLR8 antagonist.

HEK293-Blue-hTLR-9 Cells Assay

A stable HEK293-Blue-hTLR-9 cell line was purchased from InvivoGen (Cat.#: hkb-htlr9, San Diego, California, USA). These cells were originally designed for studying the stimulation of human TLR9 by monitoring the activation of NF-κB. A SEAP (secreted embryonic alkaline phosphatase) reporter gene was placed under the control of the IFN-β minimal promoter fused to five NF-κB and. AP-1-binding sites. The SEAP was induced by activating NF-κB and AP-1 via stimulating HEK-Blue hTLR9 cells with TLR9 ligands. Therefore the reporter expression was declined by TLR9 antagonist under the stimulation of a ligand, such as ODN2006 (Cat.#: tlr1-2006-1, Invivogen, San Diego, California, USA), for incubation of 20 his. The cell culture supernatant SEAP reporter activity was determined using QUANTI-Blue™ kit (Cat.#: rep-qb1, Invivogen, San Diego, California, USA) at a wavelength of 640 nm, a detection medium that turns purple or blue in the presence of alkaline phosphatase.

HEK293-Blue-hTLR9 cells were incubated at a density of 250,000-450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 p L of 20uM ODN2006 in above DMEM, perform incubation under 37° C. in a $CO_2$ incubator for 20 hrs. Then 20 μL of the supernatant from each well was incubated with 180 μL Quanti-blue substrate solution at 37° C. for 2 h and the absorbance was read at 620~655 nm using a spectrophotometer. The signaling pathway that TLR9 activation leads to downstream NF-κB activation has been widely accepted, and therefore similar reporter assay was modified for evaluating TLR9 antagonist.

The compounds of formula (I) have human TLR7 and/or TLR8 inhibitory activities ($IC_{50}$ value) <0.1 μM. Moreover, compounds of this invention also have human TLR9 inhibitory activity <0.2 μM. Activity data of the compounds of the present invention were shown in Table 1.

TABLE 1

The activity of the compounds of present invention in HEK293-Blue-hTLR-7/8/9 cells assays

| Example No | HEK/hTLR7 $IC_{50}$ (μM) | HEK/hTLR8 $IC_{50}$ (μM) | HEK/hTLR9 $IC_{50}$ (μM) |
|---|---|---|---|
| 1 | 0.053 | 0.016 | 0.039 |
| 2 | 0.087 | 0.032 | 0.065 |
| 3 | 0.019 | 0.031 | 0.093 |
| 4 | 0.016 | 0.019 | 0.137 |
| 5 | 0.012 | 0.015 | 0.084 |
| 6 | 0.067 | 0.053 | 0.139 |
| 7 | 0.030 | 0.019 | 0.120 |
| 8 | 0.078 | 0.036 | 0.073 |
| 9 | 0.051 | 0.022 | 0.047 |
| 10 | 0.069 | 0.052 | 0.041 |
| 11 | 0.050 | 0.035 | 0.096 |
| 12 | 0.087 | 0.033 | 0.060 |
| 13 | 0.056 | 0.021 | 0.132 |
| 14 | 0.080 | 0.020 | 0.116 |
| 15 | 0.067 | 0.046 | 0.094 |
| 16 | 0.035 | 0.055 | 0.075 |
| 17 | 0.088 | 0.058 | 0.103 |
| 18 | 0.060 | 0.040 | 0.119 |
| 19 | 0.057 | 0.093 | 0.116 |

Example 21

Human Microsomal Stability Assay

Human liver microsomes (Cat.NO.: 452117, Corning, USA) were preincubated with test compound for 10 minutes at 37° C. in 100 mM potassium phosphate buffer, pH 7.4. The reactions were initiated by adding NADPH regenerating system. The final incubation mixtures contained 1 μM test compound, 0.5 mg/mL liver microsomal protein, 1 mM MgCl2, 1 mM NADP, 1 unit/mL isocitric dehydrogenase and 6 mM isocitric acid in 100 mM potassium phosphate buffer, pH 7.4. After incubation times of 0, 3, 6, 9, 15 and 30 minutes at 37° C., 300 μL of cold ACN (including internal standard) was added to 100 μL incubation mixture to terminate the reaction. Following precipitation and centrifugation, 100 uL supernatant will be taken out and added 300 uL water. The amount of compound remaining in the samples was determined by LC-MS/MS. Controls of no NADPH regenerating system at zero and 30 minutes were also prepared and analyzed. Test results were summarized in Table 2.

TABLE 2

Human microsomal stability results

| Example No | Clearance of Human microsome (mL/min/kg) |
|---|---|
| 1 | 11.2 |
| 2 | 8.0 |
| 3 | 11.6 |
| 4 | 10.4 |
| 6 | 10.5 |
| 8 | 12.4 |
| 9 | 12.8 |
| 12 | 10.1 |
| 14 | 12.9 |
| 16 | 9.4 |
| 17 | 6.9 |
| 18 | 6.3 |
| 19 | 6.7 |

Example 22 hERG Channel Inhibition Assay

The hERG channel inhibition assay is a highly sensitive measurement that identifies compounds exhibiting hERG inhibition related to cardiotoxicity in vivo. The hERG K$^+$ channels were cloned in humans and stably expressed in a CHO (Chinese hamster ovary) cell line. CHO$_{hERG}$ cells were used for patch-clamp (voltage-clamp, whole-cell) experiments. Cells were stimulated by a voltage pattern to activate hERG channels and conduct I KhERG currents (rapid delayed outward rectifier potassium current of the hERG channel). After the cells were stabilized for a few minutes, the amplitude and kinetics of I KhERG were recorded at a stimulation frequency of 0.1 Hz (6 bpm). Thereafter, the test compound was added to the preparation at increasing concentrations. For each concentration, an attempt was made to reach a steady-state effect, usually, this was achieved within 3-10 min at which time the next highest concentration was applied. The amplitude and kinetics of $I_{KhERG}$ are recorded in each concentration of the drug which were compared to the control values (taken as 100%). (references: Redfern WS, Carlsson L, Davis AS, Lynch WG, MacKenzie I, Palethorpe S, Siegl PK, Strang I, Sullivan AT, Wallis R, Camm AJ, Hammond TG. 2003; Relationships between preclinical cardiac electrophysiology, clinical QT interval prolongation and torsade de pointes for a broad range of drugs: evidence for a provisional safety margin in drug development. Cardiovasc. Res. 58:32-45, Sanguinetti MC, Tristani-Firouzi M. 2006; hERG potassium channels and cardiac arrhythmia. Nature 440:463-469, Webster R, Leishman D, Walker D. 2002; Towards a drug concentration effect relationship for QT prolongation and torsades de pointes. Curr. Opin. Drug Discov. Devel. 5:116-26).

Results of hERG are given in Table 3. A safety ratio (hERG IC$_{20}$/EC$_{50}$)>30 suggests a sufficient window to differentiate the pharmacology by inhibiting TLR7/8/9 pathways from the potential hERG related cardiotoxicity.

TABLE 3 hERG results

| Example No | hERG IC20 (μM) | hERG IC50 (μM) | hERG IC20/ TLR7 IC50 | hERG IC20/ TLR8 IC50 | hERG IC20/ TLR9 IC50 |
|---|---|---|---|---|---|
| 3 | 7.4 | >20 | 383 | 240 | 79 |
| 4 | 6.3 | >20 | 384 | 355 | 45 |
| 5 | >10 | >20 | >833 | >666 | >119 |
| 10 | >10 | >20 | >145 | >197 | >242 |
| 11 | >10 | >20 | >198 | >289 | >104 |
| 16 | >10 | >20 | >289 | >182 | >134 |

Example 23

The compounds would be desirable to have minimal DDI liabilities. Therefore, the effects of compounds of formula (I) on CYP2D6 are determined.

CYP Inhibition Assay

This is a high throughput screening assay used for assessment of reversible inhibition of CYP2D6 activity of test compounds in human liver microsome (HLM) in early discovery stage.

TABLE 4

Chemicals and materials used in the CYP inhibition assay

| Substances | Description | Source | Cat. No. | Final Concentration in incubation |
|---|---|---|---|---|
| Human Liver Microsomes | | BD-Gentest | 452117 | 0.2 mg/mL |
| Dextro-methorphan | CYP2D6 substrate | Sigma | D-2531 | 5 μM |
| Dextrorphan | CYP2D6 product | | | |
| Dextrorphan-D3 | CYP2D6 internal standard | Promochem | CERD-041 | |
| Quinidine | CYP2D6 inhibitor | | | 0.5 μM |

Procedure 10 mM DMSO stock solutions of test compounds were diluted in DMSO to generate 2 mM intermediate stock solution. 250 nL of intermediate stock solution were transferred in duplicate into 3 separate 384 well microtitre plates (assay-ready plates). A mixture of HLM and each substrate was made up. 45 μL of HLM substrate mix was then transferred to each well of an assay ready plate and mixed. The negative (solvent) and positive control (standard inhibitor for CYP 2D6) were included in each assay ready plate. The assay ready plate was warmed to 37° C. in an incubator over 10 minutes. 5μL pre-warmed NADPH regenerating system was added to each incubation well to start the reaction. Final incubation volume was 50 μL. The assay plate then was placed back in the 37° C. incubator. After 10 minutes incubation, incubates were quenched by addition of 50 μL 100% acetonitrile containing internal standards (20 ng/mL D3-Dextrorphan). The supernatants were collected for RapidFire/MS/MS analysis.

RapidFire online solid phase extraction/sample injection system (Agilent) coupled with API4000 triple quadrupole mass spectrometer (AB Sciex) were used for sample analysis. The mobile phase composed of acetonitrile and water supplemented with 0.1% formic acid. A C4 solid phase extraction cartridge is used for sample separation. MS detection is achieved in positive ion MRM mode.

Data Analysis

Peak areas for substrate, metabolite and internal standard are determined using the RapidFire integrator software (version 3.6.12009.12296). Peak area ratios (PAR) of metabolite and internal standard (stable-labelled metabolite) are then calculated. The measurement window for each experiment is then defined:

PAR (0% activity)=average PAR for all incubations containing concentrated inhibitor;

Par (100% activity)=average PAR for all incubations containing no inhibitor (DMSO controls);

% Activity (test inhibitor)
=[PAR(test inhibitor)-PAR(0% activity)]/[PAR(100% activity)-PAR(0% activity)];

% Inhibition (test inhibitor)=100-% Activity (test inhibitor).

The compounds of present invention were found to have low CYP inhibition for CYP2D6 determined in the assays described above.

TABLE 5

CYP inhibition of the compounds of this invention for CYP2D6

| Example No | CYP 2D6 inhibition % @10 μM |
|---|---|
| 1 | 17 |
| 3 | -2.5 |
| 5 | 5.5 |
| 6 | 5 |
| 8 | 12.5 |
| 9 | -6.5 |
| 10 | 4.5 |
| 11 | 23 |
| 15 | 19 |
| 16 | 2 |
| 17 | 7 |
| 18 | 12.5 |
| 19 | 14.5 |

*percentage inhibition < 0: not or weak inhibitor

The invention claimed is:

1. A compound of formula (I),

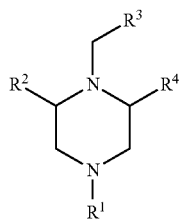

(I)

wherein:
R$^1$ is

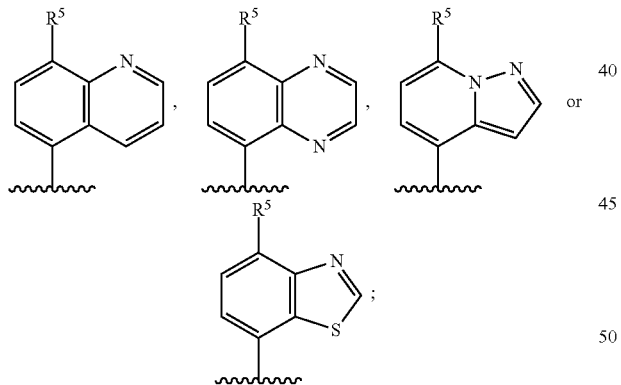

wherein R$^5$ is cyano, C$_{1-6}$alkoxy, C$_{1-6}$alkyl or halogen;
R$^2$ is C$_{1-6}$alkyl;
R$^3$ is R$^{3a}$ or —COR$^{3b}$; wherein:
R$^{3a}$ is phenyl substituted by piperazinyl and (hydroxyC$_{1-6}$ alkyl)piperazinyl, pyridinyl substituted by piperazinyl, C$_{1-6}$alkylpiperazinyl, 9-oxa-3,7-diazabicyclo[3.3.1]nonanyl, (halopyrrolidinyl)amino, (pyrrolidinylcarbonyl)piperazinyl or (((C$_{1-6}$alkyl)$_2$amino)C$_{1-6}$alkylcarbonyl)piperazinyl, or pyrimidinyl substituted by piperazinyl or (((C$_{1-6}$alkyl)$_2$amino)C$_{1-6}$alkylcarbonyl)piperazinyl;
R$^{3b}$ is 7,8-dihydro-5H-1,6-naphthyridinyl substituted by piperazinyl, 3,4-dihydro-1H-isoquinolinyl substituted by piperazinyl, isoindolinyl substituted by piperazinyl, phenylamino substituted by piperazinyl, 1,2,3,4-tetrahydroisoquinolinyl, or C$_{1-6}$ alkylpiperidinylpiperidinyl;
R$^4$ is C$_{1-6}$alkyl or H;
or a pharmaceutically acceptable salt, enantiomer or diastereomer thereof.

2. A compound of formula (I) according to claim 1, wherein:
R$^1$ is

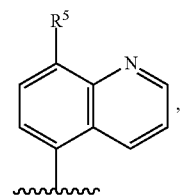

wherein R$^5$ is cyano;
or a pharmaceutically acceptable salt, enantiomer or diastereomer thereof.

3. A compound according to claim 2, wherein:
R$^2$ is methyl;
R$^3$ is R$^{3a}$ or —COR$^{3b}$; wherein:
R$^3$ is R$^{3a}$ is piperazinylphenyl ; (hydroxymethyl)piperazinylphenyl; piperazinylpyridinyl; (methylpiperazinyl)pyridinyl; 9-oxa-3 , 7-diazabicyclo[3.3.1]nonanylpyridinyl; ((fluoropyrrolidinyl)amino)pyridinyl; ((pyrrolidinylcarbonyl)piperazinyl)pyridinyl; (((dimethylamino)acetyl)piperazinyl)pyridinyl; piperazinylpyrimidinyl; or ((dimethylamino)acetyl)piperazinylpyrimidinyl;
R$^{3b}$ is piperazinyl-7,8-dihydro-5H-1,6-naphthyridinyl; piperazinyl-3,4-dihydro-1H-isoquinolinyl; piperazinylisoindolinyl; piperazinylphenylamino; 1,2,3,4-tetrahydroisoquinolinyl; or methylpiperidinylpiperidinyl;
and
R$^4$ is methyl or H;
or a pharmaceutically acceptable salt, enantiomer or diastereomer thereof.

4. A compound according to claim 2, or a pharmaceutically acceptable salt, enantiomer or diastereomer thereof, wherein:
R$^3$ is R$^{3a}$ or —COR$^{3b}$;
wherein R$^{3a}$ is pyridinyl substituted by piperazinyl; and R$^{3b}$ is isoindolinyl substituted by piperazinyl.

5. A compound selected from:
5-[(3R,5S)-3,5-Dimethyl-4-[(4-piperazin-1-ylphenyl)methyl]piperazin-1-yl]quinoline-8-carbonitrile;
4-[(3R,5R)-3,5-Dimethyl-4-[(4-piperazin-1-ylphenyl)methyl]piperazin-1-yl]quinoline-8-carbonitrile;
5-[(3R,5S)-3,5-Dimethyl-4-[(6-piperazin-1-yl-3-pyridyl)methyl]piperazin-1-yl]quinoline-8-carbonitrile;
5-[(3S,5R)-3,5-Dimethyl-4-[(5-piperazin-1-ylpyrimidin-2-yl)methyl]piperazin-1-yl]quinoline-8-carbonitrile;
5-[(3S,5R)-3,5-Dimethyl-4-[(5-piperazin-1-yl-2-pyridyl)methyl]piperazin-1-yl]quinoline-8-carbonitrile;
5-[(3S,5R)-4-[[5-[4-[2-(Dimethylamino)acetyl]piperazin-1-yl]pyrimidin-2-yl]methyl]-3,5-dimethyl-piperazin-1-yl]quinoline-8-carbonitrile;
5-[(3S,5R)-3,5-dimethyl-4-[[5-(4-methylpiperazin-1-yl)-2-pyridyl]methyl]piperazin-1-yl]quinoline-8-carbonitrile;

5-[(3S,5R)-3,5-Dimethyl-4-[[5-(9-oxa-3,7-diazabicyclo[3.3.1]nonan-3-yl)-2-pyridyl]methyl]piperazin-1-yl]quinoline-8-carbonitrile;

5-[(3R,5S)-3,5-Dimethyl-4-[[5-[[(3R,4S)-4-fluoropyrrolidin-3-yl]amino]-2-pyridyl]methyl]piperazin-1-yl]quinoline-8-carbonitrile;

5-[(3R,5S)-3,5-Dimethyl-4-[[5-[4-(pyrrolidine-2-carbonyl)piperazin-1-yl]-2-pyridyl]methyl]piperazin-1-yl]quinoline-8-carbonitrile;

5-[(3S, 5R)-4-[[5-[4-[2-(Dimethylamino)acetyl]piperazin-1-yl]-2-pyridyl]methyl]-3,5-dimethyl-piperazin-1-yl]quinoline-8-carbonitrile;

5-[(3R, 5S)-4-[[4-[2-(Hydroxymethyl)piperazin-1-yl]phenyl]methyl]-3,5-dimethyl-piperazin-1-yl]quinoline-8-carbonitrile;

5-[(3R,5S)-3,5-Dimethyl-4-[2-oxo-2-(2-piperazin-1-yl-7,8-dihydro-5H-1,6-naphthyridin-6-yl) ethyl]piperazin-1-yl]quinoline-8-carbonitrile;

5-[(3R,5S)-3,5-Dimethyl-4-[2-oxo-2-(6-piperazin-1-yl-3,4-dihydro-1H-isoquinolin-2-yl) ethyl]piperazin-1-yl]quinoline-8-carbonitrile;

5-[(3R,5S)-3,5-dimethyl-4-[2-oxo-2-(7-piperazin-1-yl-3,4-dihydro-1H-isoquinolin-2-yl) ethyl]piperazin-1-yl]quinoline-8-carbonitrile;

5-[(3R,5S)-3,5-Dimethyl-4-[2-oxo-2-(5-piperazin-1-ylisoindolin-2-yl)ethyl]piperazin-1-yl]quinoline-8-carbonitrile;

2-[4-(8-Cyano-5-quinolyl)-2-methyl-piperazin-1-yl]-N-(4-piperazin-1-ylphenyl)acetamide;

2-[4-(8-Cyano-5-quinolyl)-2-methyl-piperazin-1-yl]-N-(1,2,3,4-tetrahydroisoquinolin-6-yl) acetamide; and 5-[3-methyl-4-[2-[4-(1-methyl-4-piperidyl)-1-piperidyl]-2-oxo-ethyl]piperazin-1-yl]quinoline-8-carbonitrile;

or a pharmaceutically acceptable salt, enantiomer or diastereomer thereof.

6. A process for the preparation of a compound of formula (I) according to claim 1 comprising any of the following steps:

a) coupling reaction of a compound of formula (VI),

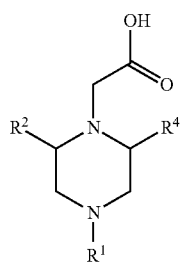

and an amine HR$^{3b}$ in the presence of a coupling reagent and a base;

b) carrying out a Buchwald-Hartwig amination reaction of a compound of formula (X),

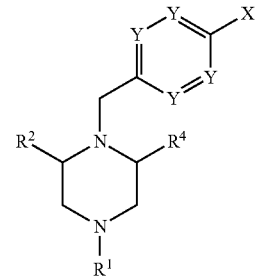

and an amine HR$^6$ in the presence of a catalyst and a base; wherein:

in step a), the coupling reagent, is HATU; and the base, is DIPEA;

in step b), the catalyst, is Ruphos Pd-G2;

the, is Cs2CO3;

X is halogen, OTf, or OMs;

Y is N or CH; R$^6$ is piperazine.

7. A pharmaceutical composition comprising a compound in accordance with claim 1 and a therapeutically inert carrier.

8. A compound or pharmaceutically acceptable salt, enantiomer or diastereomer, when manufactured according to the process of claim 6.

9. A method for the treatment of systemic lupus erythematosus or lupus nephritis, which method comprises administering to a subject in need thereof a therapeutically effective amount of a compound as defined in claim 1.

10. A method for the treatment of systemic lupus erythematosus or lupus nephritis, which method comprises administering to a subject in need thereof a therapeutically effective amount of a compound as defined in claim 5.

11. A pharmaceutical composition comprising a compound in accordance with claim 5 and a therapeutically inert carrier.

12. The process of claim 6, wherein:

R$^1$ is

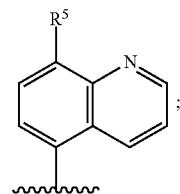

wherein R$^5$ is cyano;

R$^2$ is C$_{1-6}$alkyl; and

R$^4$ is C$_{1-6}$alkyl or H.

13. The process of claim 6, wherein:
R¹ is
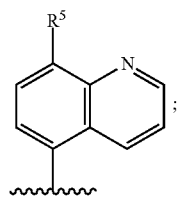
wherein R⁵ is cyano;
R² is methyl; and
R⁴ is methyl or H.
14. A compound according to claim 3, or a pharmaceutically acceptable salt, enantiomer or diastereomer thereof, wherein:
R³ is R³ᵃ or —COR³ᵇ;
  wherein R³ᵃ is pyridinyl substituted by piperazinyl; and
  R³ᵇ is isoindolinyl substituted by piperazinyl.
* * * * *